US007060265B2

(12) United States Patent
King

(10) Patent No.: US 7,060,265 B2
(45) Date of Patent: Jun. 13, 2006

(54) CLONING AND RECOMBINANT PRODUCTION OF POLISTINAE VENOM ENZYMES, SUCH AS PHOSPHOLIPASE AND HYALURONIDASE, AND IMMUNOLOGICAL THERAPIES BASED THEREON

(75) Inventor: Te Piao King, New York, NY (US)

(73) Assignee: The Rockefeller University, New York, NY (US)

( * ) Notice: Subject to any disclaimer, the term of this patent is extended or adjusted under 35 U.S.C. 154(b) by 125 days.

(21) Appl. No.: 10/688,011

(22) Filed: Oct. 17, 2003

(65) Prior Publication Data

US 2004/0175393 A1  Sep. 9, 2004

Related U.S. Application Data

(60) Division of application No. 09/806,658, filed as application No. PCT/US99/23211 on Oct. 1, 1999, now Pat. No. 6,652,851, which is a continuation-in-part of application No. 09/166,205, filed on Oct. 1, 1998, now Pat. No. 6,372,471.

(51) Int. Cl.
*A61K 38/46* (2006.01)
*C12N 9/16* (2006.01)

(52) U.S. Cl. ............... 424/94.6; 435/196; 435/198; 536/23.2

(58) Field of Classification Search ............... 424/94.6; 435/195, 196; 536/23.2, 23.1
See application file for complete search history.

(56) References Cited

U.S. PATENT DOCUMENTS 5,593,877 A   1/1997   King ............... 435/197

FOREIGN PATENT DOCUMENTS

WO   WO9400137   1/1994
WO   WO9420623   9/1994

OTHER PUBLICATIONS

Frohman, M.A. et al.; "Rapid Production of Full-Length CDNAs From Rare Transcripts: Amplification Using a Single Gene-Specific Oligonucleotide Primer"; Proceedings of the National Academy of Sciences of USA, US, National Academy of Science. Washington, vol. 85, 1998, pp. 8998-9002.

Kordis, D. and Gubensek, F.; "Ammodytoxin C Gene Helps to Elucidate the Irregular Structure of Crotaline Group II Phospholipase A2 Genes"; *European Journal of Biochemistry*, vol. 240, No. 1, Aug., 1996, pp. 83-90.

King, T.P. et al.; "Yellow Jacket Venom Allergens, Hyaluronidase and Phospholipase: Sequence Similarity and Antigenic Cross-Reactivity With Their Hornet and Wasp Homologs and Possible Implications for Clinical Allergy"; *J. Allergy Clin. Immunol.*, vol. 98, No. 3, 1996, pp. 588-600.

Mueller, U. et al.; "Successful Immunotherapy With T-Cell Epitopes of Bee Venom Phospholipase A2 (PLA) in Patients With Bee Venom (BV) Allergy"; *Journal of Allergy and Clinical Immunology*, US, Mosby-Yearly Book, Inc., vol. 97, No. 1, Part 03, Jan. 1996, p. 426.

Soldatova, L. et al.; "Sequence Similarity of a Hornet (D. Maculata) Venom Allergen Phospholipase A1 With Mammalian Lipases"; *Febs Letters*, vol. 320, 1993, pp. 145-149.

Lu, G. et al.; "Sequence Identity and Antigenic Cross-Reactivity of White Face Hornet Venom Allergen, Aldo a Hyaluronidase, With Other Proteins"; *Journal of Biological Chemistry*, vol. 270, No. 9, 1995, pp. 4457-4465.

Hoffman, D.R.; "Allergens in Hymenoptera Venom. XXVI: The Complete Amino Acid Sequence of Two Vespid Venom Phospholipases"; *International Archives of Allergy and Immunology*, vol. 104, 1994, pps. 184-190.

King, T.P. et al.; "Murine T and B Cell Responses to Natural and Recombinant Hornet Venom Allergen Dol M 5.02 and its Recombinant Fragments"; *Journal of Immunology*, US, The Williams and Wilkins Co., Baltimore, vol. 154, No. 2, 1995, pp. 577-584.

(Continued)

*Primary Examiner*—Nashaat T. Nashed
(74) *Attorney, Agent, or Firm*—Darby & Darby

(57) ABSTRACT

A unique clone of a Polistinae venom enzyme, recombinantly produced Polistinae venom enzymes, and methods of using the recombinant enzymes are provided. In a specific example, both phospholipase and hyaluronidase cDNA from *Polistes annulares* contain apparent "intronic" sequences. In still a further enbodiment, genetic engineering permits the construction of the "intronic" sequences to yield a useful coding sequence for expression of mature Polistinae venom enzyme proteins.

15 Claims, 11 Drawing Sheets

OTHER PUBLICATIONS

Forsdyke, R.; "Conservation of Stem-Loop Potential in Introns of Snake Venom Phospholipase A2 Genes: An Application of FORS-D Analysis"; *Molecular Biology and Evolution*, vol. 12, No. 6, Nov. 6, 1995, pp. 1157-1165.

Justesen, A. et al.; "Analysis of Two Incompletely Spliced Arabidopsis cDNA Encoding Novel Types of Peroxidase"; *Biochimica and Biophysica Acta*, vol. 1443, Oct. 26, 1998, pp. 149-154.

Database EMBL Nucleotide and Protein Sequences, Sep. 7, 1999, Hinxton, GB, AC=AF174528. Polistes annularis hyaluronidase precursor mRNA, partial cds. Abstract.

King, T.P. et al.; "Wasp Venom Proteins: Phospholipase A1 and B1"; *Archives of Biochemistry and Biophysics*; 1984, vol. 230, No. 1, pp. 1-12.

Suggs, et al. PNAS, USA, 78(11);6613-6617, 1981.

Edman, et al. Eur. J. Biochem., 1:80-91, 1967.

King, et al., Archives of Biochem. Biophys., 230(1):1-12, 1984.

papla, cDNA and translated amino acid sequence:

```
  I  C  F  L  L  D  D  S  T  T  F  R  N  G  T  L  N  R  G  M
ATTGCTTCTTCTTGTTAGATGATTCGACGACATTAGAAATGGTACCTTGAATAGAGGCATG    60

S  P  D  C  T  F  N  E  K  D  I  V  F  Y  V  Y  S  R  D  K
TCTCCGGATTGTACTTTTAATGAGAAAGATATAGTATTCTATGTTTACTCAAGGGATAAG   120

R  D  G  I  I  L  K  K  E  T  L  T  N  Y  D  L  F  T  K  S
CGAGAGATGGTATTATTCTTAAGAAAGAAACTTTAACGAATTACGATCTGTTTACAAAGTCT  180

T  I  S  K  Q  V  V  F  L  I  H  G  F  L  S  T  G  N  N  E
ACAATATCAAAACAAGTTGTATTTCTTATACATGGTTTCCTTTCAACTGGGAATAATGAA   240

N  F  V  A  M  S  K  A  L  I  E  K  D  D  F  L  V  I  S  V
AACTTCGTTGCTATGTCGAAAGCTTTAATAGAAAAAGATGATTTTCTTGTAATTTCGGTC   300

D  W  K  K  G  A  C  N  A  F  A  S  T  K  D  A  L  G  Y  S
GACTGGAAGAAGGGTGCTTGTAATGCTTTTGCTTCAACAAAGGATGCTTTGGGTTATTCC   360

K  A  V  G  N  T  R  H  V  G  K  F  V  A  D  F  T  K  L  L
AAAGCCGTTGGGAACACACGTCACGTTGGAAAATTTGTAGCTGATTTTACAAAACTACTT   420

V  E  K  Y  K  V  L  I  S  N  I  R  L  I  G  H  S  L  G  A
GTAGAAAAATATAAAGTGCTGATATCAAATATACGATTGATCGGGCATAGTTTGGGGCCG   480

H  T  S  G  F  A  G  K  E  V  Q  K  L  K  L  G  K  Y  K  E
CATACTTCAGGTTTTGCGGGAAAAGAAGTTCAAAAGTTAAAATTAGGAAAATACAAGGAA   540
```

Figure 1A

A ⋯⋯⋯⋯⋯ A

```
  I  I  G  L  D  P  A  G  P  Y  F  H  R  S  D  C  P  D  R  L
ATTATCGGGCTTGATCCTGCTGGACCGTATTTCATCGAGTGACTGTCCGGACAGACTT                    600

C  V  T  D  A  E  Y  V  Q  V  I  H  T  S  I  L  G  V  Y
TGCGTAACAGACGCAGAATATGTTCAAGTTATACATCAATCATATTAGGAGTATAT                       660

Y  N  V  G  S  V  D  F  Y  V  N  Y  G  K  N  Q  P  G  C  N
TATAATGTTGGTAGCGTTGATTTCTACGTGAATTATGGAAAAATCAACCTGGTTGCAAT                    720

E  P  S  C  S  H  T  K  A  V  K  Y  L  T  E  C  I  K  H  E
GAACCATCCTGCTCTCATACGAAAGCCGTGAAATATCTGACTGAGTGCATAAAACATGAA                   780

C  C  L  I  G  T  P  W  K  K  Y  F  S  T  P  K  P  I  S  Q
TGTTGTTTAATTGGAACACCATGGAAGAAATATTTCAGCACTCCAAAACCAATTTCCCAG                   840

C  R  G  D  T  C  V  C  V  G  L  N  A  K  S  Y  P  A  R  G
TGCAGAGGAGACACCTGTGTTTGCGTTGGATTGAATGCAAAAAGTTATCCTGCTAGAGGC                   900

A  F  Y  A  P  V  E  A  N  A  P  Y  C  H  N  E  G  I  K  L
GCATTTTATGCACCGGTTGAAGCAAATGCACCTTATTGCCATAACGAGGGGATTAAACTT                   960

*
TAATTATAAACAAAAGTCAATGTACACAAAAATGTATCTATTGATGAATATTAAATGAAT                   1020

AAACGAACAGTCAAATAAAAAAAAAAAAAA  1048
```

Note: The amino acid sequence ICFLL·····GTLNR represents a portion of the leader sequence, as Venom protein has the sequence of GMSPD·····

Figure 1B papla, intron 1, (between nucleotides 111-112; see papla file):

AGGTAATAATCTCGATTCTATGCGTACGCGATTTGTTGATTATTTTCAAGAAAATGTA    60

AGAAAATTTTAAAAATATATTACTGAAGTATGAAATAAAAACTTTATACTTT    114

Figure 2A papla, intron 2, (between nucleotides 720-721; see papla file):

GGTAATATTTTATATTAAAATGAACAATTCTATGGAATAGAAATAGTACAAGCATCGAT    60

TATATCCTATGCCTTGTTATATGATTCGGAGTTAGACACTATTATTTTAAATAATTTT    120

TACATTA    127

Figure 2B

Vespid plas:
- wfh, white face hornet (D. maculate); vv, yellow jacket (V. vulgaris); pa, wasp (P. annularis):

```
         1                                                                              50
wfh    ~~FSVCPFSN    DTVKMIFLTR    ATEKNFVAMS    ENRK.HDFYT    LDTMNRHNEF    KKSIIKRPVV
vv     ~~GPKCPFNS    DTVSIIIETR    ASETNFINLA    ENRN.RDLYT    LQTLQNHPEF    KKKTITRPVV
pa     GMSPDCTFNE    KDIVFYVYSR    GNNENFVAMS    DKRDGIILKK    E.TLTNYDLF    TKSTISKQVV 51                                                                             100
wfh    F.ITHGFTSS    TRLVGNFIAM    ATEKNFVAMS    EALMHTGDFL    IIMVDWRMAA    CTDEYPGLKY
vv     F.ITHGFTSS    TRLVGQYIAT    ASETNFINLA    KALVDKDNYM    VISIDWQTAA    CTNEAAGLKY
pa     FLI.HGFLST    TRHVGKFVAD    GNNENFVAMS    KALIEKDDFL    VISVDWKKGA    C.NAFASTKD 101                                                                            150
wfh    .MFYKAAVGN    GKFSEIIGLD    IAKKLVEQYK    VPMTNIRLVG    HSLGAHISGF
vv     .LYYPTAARN    GKFSEIIGLD    ITQKLVKHYK    ISMANIRLIG    HSLGAHISGF
pa     ALGYSKAVGN    GKFKEIIGLD    FTKLLVEKYK    VLISNIRLIG    HSLGAHISGF 151                                                                            200
wfh    AGKRVQELKL    GKFSEIIGLD    PAGPSFKKND    CSERICETDA    HYVQILHTSS
vv     AGKRVQELKL    GKFSEIIGLD    PARPSFDSNH    CSERLCETDA    EYVQIIHTSN
pa     AGKRVQELKL    GKFKEIIGLD    PAGPYFHRSD    CPDRLCVTDA    EYVQVIHTSI
```

Figure 3A

```
        201
wfh     NLGTERTLGT  VDFYINNGSN  QPGCRYIIGE  TCSHTRAVKY  FTECIRRECC
vv      TLGTEKTLGT  VDFYMNNGKN  QPGGGRFFSE  VCSHSRAVIY  MAECIKHECC
pa      ILGVYYNVGS  VDFYVNYGKN  QPGCNEPS..  .CSHTKAVKY  LTECIKHECC 251                                                     300
wfh     LIGVPQSK..  .SPQPVSKCT  RNECVCVGLN  AKKYPKRGSF  YVPVEAEAPY
vv      LIGIPKSK..  .SSQPISSCT  KQECVCVGLN  AKKYPSRGSF  YVPVESTAPF
pa      LIGTPWKKYF  STPKPISQCR  GDTCVCVGLN  AKSYPARGAF  YAPVEANAPY 301
wfh     CNNNGKII
vv      CNNKGKII
pa      CHNEGIKL
```

Figure 3B

Pahya, cDNA and translated amino acid sequence:

```
                       Y  V  S  L  S  P  D  S  V  F  N
                     TATGTGTCATTGTCCCCGACTCAGTATTTAA          480

I  I  T  D  D  I  S  H  Q  I  L  S  R  S  N  C  E  R  S  K
TATCATCACCGATGACATCTCCCACCAAATTCTTTCCAGATCGAATTGTGAAAGATCCAA   540

R  P  K  R  V  F  S  I  Y  W  N  V  P  T  F  N  C  H  Q  Y
AAGACCGAAAAGGGTCTTCAGCATTTATTGGAACGTTCCTACCTTTATGTGCCACCAATA   600

G  M  N  F  D  E  V  T  D  F  N  I  K  H  N  S  K  D  N  F
TGGCATGAATTCGACGAGGTGACAGATTTAATATCAAACATAATTCTAAGGACAATTT    660

R  G  E  T  I  S  I  Y  Y  D  P  G  K  F  P  A  L  M  P  L
TCGCGGTGAAACTATATCAATTTATTACGATCCTGGAAAATTCCAGCATTGATGCCACT   720

K  N  G  N  Y  E  E  R  N  G  G  V  P  Q  R  G  N  I  T  I
AAAAAATGGTAATTATGAGGAAAGAAACGGAGGGTTCCTCAGCGAGGTAACATCACGAT   780

H  L  Q  Q  F  N  E  D  L  D  K  M  T  P  D  K  N  F  G  G
ACATTTGCAACAATTTAACGAAGATTGGATAAAATGACACCGGATAAAAATTTCGGTGG   840

I  G  V  I  D  F  E  R  W  K  P  I  F  R  Q  N  W  G  N  T
TATCGGTGTAATCGATTTCGAAAGATGGAAACCGATTTCCGACAGAATTGGGGTAACAC   900

E  I  H  K  K  Y  S  I  E  L  V  R  K  E  H  P  K  W  S  E
GGAAATACATAAGAAATATTCTATTGAACTCGTTCGGAAAGAACATCCAAAGTGGAGCGA  960
```

Figure 4A

```
        S   M   I   E   A   E   A   T   K   K   F   E   K   Y   A   R   Y   F   M   E
     ATCGATGATCGAAGCGGAAGCTACGAAAAAGTTCGAGAAATATGCGAGATATTCATGGA         1020

E   T   L   K   L   A   K   K   T   R   K   R   A   K   W   G   Y   Y   G   F
     AGAAACTTTGAAATTGGCAAAAAAGACTAGGAAAAGGGCTAAGTGGGTTATACGGATT         1080

P   Y   C   Y   N   V   T   P   N   N   P   G   P   D   C   D   A   K   A   T
     TCCTTACTGCTATAACGTAACACCGAATAATCCTGGCCCGGATTGCGATGCTAAAGGAC         1140

I   E   N   D   R   L   S   W   M   Y   N   N   Q   E   I   L   F   P   S   V
     AATCGAGAACGATAGACTGTCGTGGATGTACAATAATCAAGAAATACTTTTCCATCCGT         1200

Y   V   R   H   E   Q   K   P   E   E   R   V   Y   L   V   Q   G   R   I   K
     CTACGTGAGACATGAACAAAAACCGGAGGAAAGGGTTTACCTAGTGCAAGGTAGAATTAA         1260

E   A   V   R   I   S   N   N   L   E   H   S   P   S   V   L   A   Y   W   W
     AGAAGCTGTTAGGATATCGAATAATTTAGAACATTCACCTAGTGTGCTTGCTTATTGGTG      1320

Y   V   Y   Q   D   K   M   D   I   Y   L   S   E   T   D   V   E   K   T   F
     GTACGTGTATCAGGACAAGATGGACATTTACCTAAGCGAGACCGACGTGGAAAAGACTTT     1380
```

Figure 4B

```
Q  E  I  V  T  N  G  G  D  G  I  I  I  W  G  S  S  S  D  V
CCAAGAGATAGTGACTAATGGTGGGGATGGTATCATAATATGGGGTAGCTCGTCCGATGT                1440

N  S  L  S  K  C  K  R  L  R  E  Y  L  L  N  T  L  G  P  F
TAACAGCCTAAGTGTAAGAGATTGAGAGAGTACCTGTTAAACACTTTAGGACCGTT                    1500

A  V  N  V  T  E  T  V  N  G  R  S  S  L  N  F  *
CGGGGTTAATGTAACAGAAACTGTCAACGGAAGATCATCCCTAAACTTCTAAATAATCG                 1560

ATAACGCCTAATCACGTCGATGATGATTATTAGGGTGTTCTTCGGTGATGGTTTGATCT                 1620

CACTGAAAAGACTTTCGTTAAAAAACAAAAAGATAAATGTAATTTATAAGTTAAAAAAA                 1680

CCTATACGACCAAAGAAAGAAAGAAAAAAAAAAAAAAAAA

Note: The amino acid sequence YVSLSP.....RSNCER represents a portion of the leader sequence as
      the venom protein has the sequence of SKRPKR.....
```

Figure 4C pahya, intron sequence, (between nucleotides 733 and 734):

ATTTTCTACTACAGTTCTTTTTATCTCTCTATCATTGATGATAAATCGTTAAATCGAT    60

CTATTGTAAATTATCTATCGATTGTTTAGGCAAA    94

Figure 5

Vespid hyas:

```
          1
wfh   SERPKRVFNI  YWNVPTFMCH  QYGLYFDEVT  N.FNIKHNSK  DDFQGDKISI
vv    SERPKRVFNI  YWNVPTFMCH  QYDLYFDEVT  N.FNIKRNSK  DDFQGDKIAI
pa    SERPKRVFSI  YWNVPTFMCH  QYGMNFDEVT  D.FNIKHNSK  DNFRGETISI
bv    NNKTVREFNV  YWNVPTFMCH  KYGLRFEEVS  EKYGILQNWM  DKFRGEEIAI 51                                                      100
wfh   FYDPGEFPAL  LPLKEGNYKI  RNGGVPQEGN  ITIHLQRFIE  NLDKTYPNRN
vv    FYDPGEFPAL  LSLKDGKYKK  RNGGVPQEGN  ITIHLQKFIE  NLDKIYPNRN
pa    YYDPGKFPAL  MPLKNGNYEE  RNGGVPQRGN  ITIHLQQFNE  DLDKMTPDKN
bv    LYDPGMFPAL  LKDPNGNVVA  RNGGVPQLGN  LTKHLQVFRD  HLINQIPDKS 101                                                     150
wfh   FNGIGVIDFE  RWRPIFRQNW  GNMMIHKKFS  IDLVRNEHPF  WDKKMIELEA
vv    FSGIGVIDFE  RWRPIFRQNW  GNMKIHKNFS  IDLVRNEHPT  WNKKMIELEA
pa    FGGIGVIDFE  RWKPIFRQNW  GNTEIHKKYS  IELVRKEHPK  WSESMIEAEA
bv    FPGVGVIDFE  SWRPIFRQNW  ASLQPYKKLS  VEVVRREHPF  WDDQRVEQEA 151                                                     200
wfh   SKRFEKYARL  FMEETLKLAK  KTRKQADWGY  YGYPYCFNMS  PNNLVPDCDA
vv    SKRFEKYARF  FMEETLKLAK  KTRKQADWGY  YGYPYCFNMS  PNNLVPECDV
pa    TKKFEKYARY  FMEETLKLAK  KTRKRAKWGY  YGFPYCYNVT  PNNPGPDCDA
bv    KRRFEKYGQL  FMEETLKAAK  RMRPAANWGY  YAYPYCYNLT  PNQPSAQCEA
```

Figure 6A

```
       251
wfh    NLKHS.PKVL  SYWWYVYQDD  TNTFLTETDV  KKTFQEIAIN  GGDGIIIWGS
vv     NLKHS.PKVL  SYWWYVYQDE  TNTFLTETDV  KKTFQEIVIN  GGDGIIIWGS
pa     NLKHS.PKVL  AYWWYVYQDK  MDIYLSETDV  EKTFQEIVTN  GGDGIIIWGS
bv     QMTTSRKKVL  PYYWYKYQDR  RDTDLSRADL  EATLRKITDL  GGDGIIIWGS 301
wfh    SSDVNSLSKC  KRLREYLLTV  LGPITVNVTE  TVN~~~~~~   ~~~~~~
vv     SSDVNSLSKC  KRLQDYLLTV  LGPIANINVTE AVN~~~~~~   ~~~~~~
pa     SSDVNSLSKC  KRLREYLLNT  LGPFAVNVTE  TVNGRSSLNF  ~~~~~~
bv     SDDINTKAKC  LQFREYLNNE  LGPAVKRIAL  NNNANDRLTV  DVSVDQV*
```

Figure 6B

SEQUENCE LISTING

<160> NUMBER OF SEQ ID NOS: 12

<210> SEQ ID NO 1
<211> LENGTH: 1048
<212> TYPE: DNA
<213> ORGANISM: Polistes annularis

<400> SEQUENCE: 1

```
atttgcttct tgttagatga ttcgacgaca tttagaaatg gtaccttgaa tagaggcatg      60
tctccggatt gtacttttaa tgagaaagat atagtattct atgtttactc aagggataag     120
cgagatggta ttattcttaa gaaagaaact ttaacgaatt acgatctgtt tacaaagtct     180
acaatatcaa aacaagttgt atttcttata catggtttcc tttcaactgg gaataatgaa     240
aacttcgttg ctatgtcgaa agctttaata gaaaagatg attttcttgt aatttcggtc     300
gactggaaga agggtgcttg taatgctttt gcttcaacaa aggatgcttt gggttattcc     360
aaagccgttg gaaacacacg tcacgttgga aaatttgtag ctgattttac aaaactactt     420
gtagaaaaat ataaagtgct gatatcaaat atacgattga tcgggcatag tttgggcgcg     480
catacttcag gttttgcggg aaaagaagtt caaaagttaa aattaggaaa atacaaggaa     540
attatcgggc ttgatcctgc tggaccgtat tttcatcgga gtgactgtcc ggacagactt     600
tgcgtaacag acgcagaata tgttcaagtt atacatacat caatcatatt aggagtatat     660
tataatgttg gtagcgttga tttctacgtg aattatggaa aaaatcaacc tggttgcaat     720
gaaccatcct gctctcatac gaaagccgtg aaatatctga ctgagtgcat aaaacatgaa     780
tgttgtttaa ttggaacacc atggaagaaa tatttcagca ctccaaaacc aatttcccag     840
tgcagaggag acacctgtgt ttgcgttgga ttgaatgcaa aaagttatcc tgctagaggc     900
gcattttatg caccggttga agcaaatgca ccttattgcc ataacgaggg gattaaactt     960
taattataaa caaaagtcaa tgtacacaaa aatgtatcta ttgatgaata ttaaatgaat    1020
aaacgaacag tcaaataaaa aaaaaaaa                                        1048
```

<210> SEQ ID NO 2
<211> LENGTH: 320
<212> TYPE: PRT

<213> ORGANISM: Polistes annularis

<400> SEQUENCE: 2

```
Ile Cys Phe Leu Leu Asp Asp Ser Thr Thr Phe Arg Asn Gly Thr Leu
1               5                   10                  15
Asn Arg Gly Met Ser Pro Asp Cys Thr Phe Asn Glu Lys Asp Ile Val
            20                  25                  30
Phe Tyr Val Tyr Ser Arg Asp Lys Arg Asp Gly Ile Ile Leu Lys Lys
        35                  40                  45
Glu Thr Leu Thr Asn Tyr Asp Leu Phe Thr Lys Ser Thr Ile Ser Lys
    50                  55                  60
Gln Val Val Phe Leu Ile His Gly Phe Leu Ser Thr Gly Asn Asn Glu
65                  70                  75                  80
Asn Phe Val Ala Met Ser Lys Ala Leu Ile Glu Lys Asp Phe Leu
                85                  90                  95
Val Ile Ser Val Asp Trp Lys Lys Gly Ala Cys Asn Ala Phe Ala Ser
            100                 105                 110
Thr Lys Asp Ala Leu Gly Tyr Ser Lys Ala Val Gly Asn Thr Arg His
        115                 120                 125
Val Gly Lys Phe Val Ala Asp Phe Thr Lys Leu Leu Val Glu Lys Tyr
    130                 135                 140
Lys Val Leu Ile Ser Asn Ile Arg Leu Ile Gly His Ser Leu Gly Ala
145                 150                 155                 160
His Thr Ser Gly Phe Ala Gly Lys Glu Val Gln Lys Leu Lys Leu Gly
                165                 170                 175
Lys Tyr Lys Glu Ile Ile Gly Leu Asp Pro Ala Gly Pro Tyr Phe His
            180                 185                 190
Arg Ser Asp Cys Pro Asp Arg Leu Cys Val Thr Asp Ala Glu Tyr Val
        195                 200                 205
Gln Val Ile His Thr Ser Ile Ile Leu Gly Val Tyr Tyr Asn Val Gly
    210                 215                 220
Ser Val Asp Phe Tyr Val Asn Tyr Gly Lys Asn Gln Pro Gly Cys Asn
225                 230                 235                 240
Glu Pro Ser Cys Ser His Thr Lys Ala Val Lys Tyr Leu Thr Glu Cys
                245                 250                 255
Ile Lys His Glu Cys Cys Leu Ile Gly Thr Pro Trp Lys Lys Tyr Phe
            260                 265                 270
Ser Thr Pro Lys Pro Ile Ser Gln Cys Arg Gly Asp Thr Cys Val Cys
        275                 280                 285
Val Gly Leu Asn Ala Lys Ser Tyr Pro Ala Arg Gly Ala Phe Tyr Ala
    290                 295                 300
Pro Val Glu Ala Asn Ala Pro Tyr Cys His Asn Glu Gly Ile Lys Leu
305                 310                 315                 320
```

<210> SEQ ID NO 3
<211> LENGTH: 1273
<212> TYPE: DNA
<213> ORGANISM: Polistes annularis

<400> SEQUENCE: 3

```
tatgtgtcat tgtcccccga ctcagtattt aatatcatca ccgatgacat ctcccaccaa      60
attctttcca gatcgaattg tgaaagatcc aaaagaccga aagggtctt cagcatttat     120 tggaacgttg ctacctttat gtgccaccaa tatggcatga atttcgacga ggtgacagat     180
tttaatatca aacataattc taaggacaat tttcgcggtg aaactatatc aatttattac     240
```

```
gatcctggaa aatttccagc attgatgcca ctaaaaaatg gtaattatga ggaaagaaac    300 ggagggggttc ctcagcgagg taacatcacg atacatttgc aacaatttaa cgaagatttg    360
gataaaatga caccggataa aaatttcggt ggtatcggtg taatcgattt cgaaagatgg    420
aaaccgattt tccgacagaa ttggggtaac acggaaatac ataagaaata ttctattgaa    480
ctcgttcgga aagaacatcc aaagtggagc aatcgatga tcgaagcgga agctacgaaa    540
aagttcgaga atatgcgag atatttcatg gaagaaactt tgaaattggc aaaaaagact    600
aggaaaaggg ctaagtgggg ttattacgga tttccttact gctataacgt aacaccgaat    660
aatcctggcc cggattgcga tgctaaagcg acaatcgaga acgatagact gtcgtggatg    720
tacaataatc aagaaatact ttttccatcc gtctacgtga acatgaaca aaaaccggag    780 gaaagggttt acctagtgca aggtagaatt aaagaagctg ttaggatatc gaataattta    840
gaacattcac ctagtgtgct tgcttattgg tggtacgtgt atcaggacaa gatggacatt    900
tacctaagcg agaccgacgt ggaaaagact ttccaagaga tagtgactaa tggtggggat    960
ggtatcataa tatggggtag ctcgtccgat gttaacagcc taagtaaatg taagagattg    1020
agagagtacc tgttaaacac tttaggaccg ttcgcggtta atgtaacaga aactgtcaac    1080
ggaagatcat ccctaaactt ctaaaataat cgataacgcc taatcacgtc gatgatgatt    1140
attagggtgt tcttcggtga ttggtttgat ctcactgaaa agacttttcg ttaaaaaaca    1200 aaagataaa tgtaatttat aagttaaaaa aacctatacg accaaagaaa gaaagaaaaa    1260
aaaaaaaaaa aaa                                                       1273

<210> SEQ ID NO 4
<211> LENGTH: 367
<212> TYPE: PRT
<213> ORGANISM: Polistes annularis

<400> SEQUENCE: 4

Tyr Val Ser Leu Ser Pro Asp Ser Val Phe Asn Ile Ile Thr Asp Asp
1               5                   10                  15

Ile Ser His Gln Ile Leu Ser Arg Ser Asn Cys Glu Arg Ser Lys Arg
                20                  25                  30

Pro Lys Arg Val Phe Ser Ile Tyr Trp Asn Val Pro Thr Phe Met Cys
            35                  40                  45

His Gln Tyr Gly Met Asn Phe Asp Glu Val Thr Asp Phe Asn Ile Lys
        50                  55                  60

His Asn Ser Lys Asp Asn Phe Arg Gly Glu Thr Ile Ser Ile Tyr Tyr
65                  70                  75                  80

Asp Pro Gly Lys Phe Pro Ala Leu Met Pro Leu Lys Asn Gly Asn Tyr
                85                  90                  95

Glu Glu Arg Asn Gly Gly Val Pro Gln Arg Gly Asn Ile Thr Ile His
            100                 105                 110

Leu Gln Gln Phe Asn Glu Asp Leu Asp Lys Met Thr Pro Asp Lys Asn
        115                 120                 125

Phe Gly Gly Ile Gly Val Ile Asp Phe Glu Arg Trp Lys Pro Ile Phe
    130                 135                 140

Arg Gln Asn Trp Gly Asn Thr Glu Ile His Lys Lys Tyr Ser Ile Glu
145                 150                 155                 160

Leu Val Arg Lys Glu His Pro Lys Trp Ser Glu Ser Met Ile Glu Ala
                165                 170                 175

Glu Ala Thr Lys Lys Phe Glu Lys Tyr Ala Arg Tyr Phe Met Glu Glu
```

-continued

```
                180                 185                 190
Thr Leu Lys Leu Ala Lys Lys Thr Arg Lys Arg Ala Lys Trp Gly Tyr
            195                 200                 205
Tyr Gly Phe Pro Tyr Cys Tyr Asn Val Thr Pro Asn Asn Pro Gly Pro
        210                 215                 220
Asp Cys Asp Ala Lys Ala Thr Ile Glu Asn Asp Arg Leu Ser Trp Met
225                 230                 235                 240
Tyr Asn Asn Gln Glu Ile Leu Phe Pro Ser Val Tyr Val Arg His Glu
                245                 250                 255
Gln Lys Pro Glu Glu Arg Val Tyr Leu Val Gln Gly Arg Ile Lys Glu
            260                 265                 270
Ala Val Arg Ile Ser Asn Asn Leu Glu His Ser Pro Ser Val Leu Ala
        275                 280                 285
Tyr Trp Trp Tyr Val Tyr Gln Asp Lys Met Asp Ile Tyr Leu Ser Glu
    290                 295                 300
Thr Asp Val Glu Lys Thr Phe Gln Glu Ile Val Thr Asn Gly Gly Asp
305                 310                 315                 320
Gly Ile Ile Ile Trp Gly Ser Ser Ser Asp Val Asn Ser Leu Ser Lys
                325                 330                 335
Cys Lys Arg Leu Arg Glu Tyr Leu Leu Asn Thr Leu Gly Pro Phe Ala
            340                 345                 350
Val Asn Val Thr Glu Thr Val Asn Gly Arg Ser Ser Leu Asn Phe
        355                 360                 365
```

<210> SEQ ID NO 5
<211> LENGTH: 114
<212> TYPE: DNA
<213> ORGANISM: Polistes annularis

<400> SEQUENCE: 5

```
aggtaataat ctcgattcta tgcgtacgcg attttgttga ttattttca agaaaatgta      60
agaaaaattt ttaaaaatat attactgaag tatgaaataa aaactttata cttt          114
```

<210> SEQ ID NO 6
<211> LENGTH: 127
<212> TYPE: DNA
<213> ORGANISM: Polistes annularis

<400> SEQUENCE: 6

```
ggtaatattt ttatattaaa atgaacaatt ctatggaata gaaatagtac aagcatcgat      60
tatatcctat gccttgttat atgatttcgg agttagacac tattattttt aaataatttt    120
tacatta                                                              127
```

<210> SEQ ID NO 7
<211> LENGTH: 317
<212> TYPE: PRT
<213> ORGANISM: Dolichovespula maculata

<400> SEQUENCE: 7

```
Arg Leu Ile Met Phe Val Gly Asp Pro Ser Ser Asn Glu Leu Asp
1               5                   10                  15
Arg Phe Ser Val Cys Pro Phe Ser Asn Asp Thr Val Lys Met Ile Phe
            20                  25                  30
Leu Thr Arg Glu Asn Arg Lys His Asp Phe Tyr Thr Leu Asp Thr Met
        35                  40                  45
Asn Arg His Asn Glu Phe Lys Lys Ser Ile Ile Lys Arg Pro Val Val
```

```
                50                  55                  60
Phe Ile Thr His Gly Phe Thr Ser Ser Ala Thr Glu Lys Asn Phe Val
 65                  70                  75                  80

Ala Met Ser Glu Ala Leu Met His Thr Gly Asp Phe Leu Ile Ile Met
                 85                  90                  95

Val Asp Trp Arg Met Ala Ala Cys Thr Asp Glu Tyr Pro Gly Leu Lys
            100                 105                 110

Tyr Met Phe Tyr Lys Ala Ala Val Gly Asn Thr Arg Leu Val Gly Asn
            115                 120                 125

Phe Ile Ala Met Ile Ala Lys Lys Leu Val Gln Tyr Lys Val Pro
        130                 135                 140

Met Thr Asn Ile Arg Leu Val Gly His Ser Leu Gly Ala His Ile Ser
145                 150                 155                 160

Gly Phe Ala Gly Lys Arg Val Gln Glu Leu Lys Leu Gly Lys Phe Ser
                165                 170                 175

Glu Ile Ile Gly Leu Asp Pro Ala Gly Pro Ser Phe Lys Lys Asn Asp
            180                 185                 190

Cys Ser Glu Arg Ile Cys Glu Thr Asp Ala His Tyr Val Gln Ile Leu
        195                 200                 205

His Thr Ser Ser Asn Leu Gly Thr Glu Arg Thr Leu Gly Thr Val Asp
    210                 215                 220

Phe Tyr Ile Asn Asn Gly Ser Asn Gln Pro Gly Cys Arg Tyr Ile Ile
225                 230                 235                 240

Gly Glu Thr Cys Ser His Thr Arg Ala Val Lys Tyr Phe Thr Glu Cys
                245                 250                 255

Ile Arg Arg Glu Cys Cys Leu Ile Gly Val Pro Gln Ser Lys Asn Pro
            260                 265                 270

Gln Pro Val Ser Lys Cys Thr Arg Asn Glu Cys Val Cys Val Gly Leu
        275                 280                 285

Asn Ala Lys Lys Tyr Pro Lys Arg Gly Ser Phe Tyr Val Pro Val Glu
    290                 295                 300

Ala Glu Ala Pro Tyr Cys Asn Asn Asn Gly Lys Ile Ile
305                 310                 315

<210> SEQ ID NO 8
<211> LENGTH: 300
<212> TYPE: PRT
<213> ORGANISM: Vespula vulgaris

<400> SEQUENCE: 8

Gly Pro Lys Cys Pro Phe Asn Ser Asp Thr Val Ser Ile Ile Ile Glu
 1               5                  10                  15

Thr Arg Glu Asn Arg Asn Arg Asp Leu Tyr Thr Leu Gln Thr Leu Gln
                20                  25                  30

Asn His Pro Glu Phe Lys Lys Lys Thr Ile Thr Arg Pro Val Val Phe
            35                  40                  45

Ile Thr His Gly Phe Thr Ser Ser Ala Ser Glu Thr Asn Phe Ile Asn
        50                  55                  60

Leu Ala Lys Ala Leu Val Asp Lys Asp Asn Tyr Met Val Ile Ser Ile
 65                  70                  75                  80

Asp Trp Gln Thr Ala Ala Cys Thr Asn Glu Ala Ala Gly Leu Lys Tyr
                85                  90                  95

Leu Tyr Tyr Pro Thr Ala Ala Arg Asn Thr Arg Leu Val Gly Gln Tyr
            100                 105                 110
```

-continued

```
Ile Ala Thr Ile Thr Gln Lys Leu Val Lys His Tyr Lys Ile Ser Met
        115                 120                 125

Ala Asn Ile Arg Leu Ile Gly His Ser Leu Gly Ala His Ala Ser Gly
    130                 135                 140

Phe Ala Gly Lys Lys Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Thr Leu Gly Thr Val Asp Phe
        195                 200                 205

Tyr Met Asn Asn Gly Lys Asn Gln Pro Gly Cys Gly Arg Phe Phe Ser
210                 215                 220

Glu Val Cys Ser His Ser Arg Ala Val Ile Tyr Met Ala Glu Cys Ile
225                 230                 235                 240

Lys His Glu Cys Cys Leu Ile Gly Ile Pro Lys Ser Lys Ser Ser Gln
                245                 250                 255

Pro Ile Ser Ser Cys Thr Lys Gln Glu Cys Val Cys Val Gly Leu Asn
            260                 265                 270

Ala Lys Lys Tyr Thr Ser Arg Gly Ser Phe Tyr Val Pro Val Glu Ser
        275                 280                 285

Thr Val Pro Phe Cys Asn Asn Lys Gly Lys Ile Ile
        290                 295                 300
```

<210> SEQ ID NO 9
<211> LENGTH: 94
<212> TYPE: DNA
<213> ORGANISM: Polistes annularis

<400> SEQUENCE: 9
atttttctac tacagttctt tttatctctc tatcattgat gataaatcgt ttaaatcgat    60
ctattgtaaa ttatctatcg attgtttagg caaa                               94

<210> SEQ ID NO 10
<211> LENGTH: 347
<212> TYPE: PRT
<213> ORGANISM: Apis melliferis

<400> SEQUENCE: 10

```
Asn Asn Lys Thr Val Arg Glu Phe Asn Val Tyr Trp Asn Val Pro Thr
1               5                   10                  15

Phe Met Cys His Lys Tyr Gly Leu Arg Phe Glu Glu Val Ser Glu Lys
            20                  25                  30

Tyr Gly Ile Leu Gln Asn Trp Met Asp Lys Phe Arg Gly Glu Glu Ile
        35                  40                  45

Ala Ile Leu Tyr Asp Pro Gly Met Phe Pro Ala Leu Leu Lys Asp Pro
    50                  55                  60

Asn Gly Asn Val Val Ala Arg Asn Gly Val Pro Gln Leu Gly Asn
65                  70                  75                  80

Leu Thr Lys His Leu Gln Val Phe Arg Asp His Tyr Ile Asn Gln Ile
            85                  90                  95

Pro Asp Lys Ser Phe Pro Gly Val Gly Val Ile Asp Phe Glu Ser Trp
            100                 105                 110

Arg Pro Ile Phe Arg Gln Asn Trp Ala Ser Leu Gln Pro Tyr Lys Lys
        115                 120                 125
```

-continued

```
Leu Ser Val Glu Val Val Arg Arg Glu His Pro Phe Trp Asp Asp Gln
        130                 135                 140

Arg Val Glu Gln Glu Ala Lys Arg Arg Phe Glu Lys Tyr Gly Gln Leu
145                 150                 155                 160

Phe Met Glu Glu Thr Leu Lys Ala Ala Lys Arg Met Arg Pro Ala Ala
                165                 170                 175

Asn Trp Gly Tyr Tyr Ala Tyr Pro Tyr Cys Tyr Asn Leu Thr Pro Asn
            180                 185                 190

Gln Pro Ser Ala Gln Cys Glu Ala Thr Thr Met Gln Glu Asn Asp Lys
        195                 200                 205

Met Ser Trp Leu Phe Glu Ser Glu Asp Val Leu Leu Pro Ser Val Tyr
210                 215                 220

Leu Arg Trp Asn Leu Thr Ser Gly Glu Arg Val Gly Leu Val Gly Gly
225                 230                 235                 240

Arg Val Lys Glu Ala Leu Arg Ile Ala Arg Gln Met Thr Thr Ser Arg
                245                 250                 255

Lys Lys Val Leu Pro Tyr Tyr Trp Tyr Lys Tyr Gln Asp Arg Arg Asp
            260                 265                 270

Thr Asp Leu Ser Arg Ala Asp Leu Glu Ala Thr Leu Arg Lys Ile Thr
        275                 280                 285

Asp Leu Gly Ala Asp Gly Phe Ile Ile Trp Gly Ser Ser Asp Asp Ile
290                 295                 300

Asn Thr Lys Ala Lys Cys Leu Gln Phe Arg Glu Tyr Leu Asn Asn Glu
305                 310                 315                 320

Leu Gly Pro Ala Val Lys Arg Ile Ala Leu Asn Asn Ala Asn Asp
                325                 330                 335

Arg Leu Thr Val Asp Val Ser Val Asp Gln Val
            340                 345

<210> SEQ ID NO 11
<211> LENGTH: 331
<212> TYPE: PRT
<213> ORGANISM: Dolichovespula maculata

<400> SEQUENCE: 11

Ser Glu Arg Pro Lys Arg Val Phe Asn Ile Tyr Trp Asn Val Pro Thr
1               5                   10                  15

Phe Met Cys His Gln Tyr Gly Leu Tyr Phe Asp Glu Val Thr Asn Phe
                20                  25                  30

Asn Ile Lys His Asn Ser Lys Asp Asp Phe Gln Gly Asp Lys Ile Ser
            35                  40                  45

Ile Phe Tyr Asp Pro Gly Glu Phe Pro Ala Leu Leu Pro Leu Lys Glu
        50                  55                  60

Gly Asn Tyr Lys Ile Arg Asn Gly Gly Val Pro Gln Glu Gly Asn Ile
65                  70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
            100                 105                 110

Pro Ile Phe Arg Gln Asn Trp Gly Asn Met Met Ile His Lys Lys Phe
        115                 120                 125

Ser Ile Asp Leu Val Arg Asn Glu His Pro Phe Trp Asp Lys Lys Met
130                 135                 140

Ile Glu Leu Glu Ala Ser Lys Arg Phe Glu Lys Tyr Ala Arg Leu Phe
```

```
             145                 150                 155                 160
Met Glu Glu Thr Leu Lys Leu Ala Lys Lys Thr Arg Lys Gln Ala Asp
                165                 170                 175
Trp Gly Tyr Tyr Gly Tyr Pro Tyr Cys Phe Asn Met Ser Pro Asn Asn
            180                 185                 190
Leu Val Pro Asp Cys Asp Ala Thr Ala Met Leu Glu Asn Asp Lys Met
            195                 200                 205
Ser Trp Leu Phe Asn Asn Gln Asn Val Leu Pro Ser Val Tyr Ile
            210                 215                 220
Arg His Glu Leu Thr Pro Asp Gln Arg Val Gly Leu Val Gln Gly Arg
225                 230                 235                 240
Val Lys Glu Ala Val Arg Ile Ser Asn Asn Leu Lys His Ser Pro Lys
                245                 250                 255
Val Leu Ser Tyr Trp Trp Tyr Val Tyr Gln Asp Asp Thr Asn Thr Phe
                260                 265                 270
Leu Thr Glu Thr Asp Val Lys Lys Thr Phe Gln Glu Ile Ala Ile Asn
            275                 280                 285
Gly Gly Asp Gly Ile Ile Ile Trp Gly Ser Ser Ser Asp Val Asn Ser
290                 295                 300
Leu Ser Lys Cys Lys Arg Leu Arg Glu Tyr Leu Leu Thr Val Leu Gly
305                 310                 315                 320
Pro Ile Thr Val Asn Val Thr Glu Thr Val Asn
                325                 330

<210> SEQ ID NO 12
<211> LENGTH: 331
<212> TYPE: PRT
<213> ORGANISM: Vespula vulgaris

<400> SEQUENCE: 12

Ser Glu Arg Pro Lys Arg Val Phe Asn Ile Tyr Trp Asn Val Pro Thr
1               5                   10                  15
Phe Met Cys His Gln Tyr Asp Leu Tyr Phe Asp Glu Val Thr Asn Phe
                20                  25                  30
Asn Ile Lys Arg Asn Ser Lys Asp Asp Phe Gln Gly Asp Lys Ile Ala
            35                  40                  45
Ile Phe Tyr Asp Pro Gly Glu Phe Pro Ala Leu Leu Ser Leu Lys Asp
        50                  55                  60
Gly Lys Tyr Lys Lys Arg Asn Gly Gly Val Pro Gln Glu Gly Asn Ile
65                  70                  75                  80
Thr Ile His Leu Gln Lys Phe Ile Glu Asn Leu Asp Lys Ile Tyr Pro
                85                  90                  95
Asn Arg Asn Phe Ser Gly Ile Gly Val Ile Asp Phe Glu Arg Trp Arg
                100                 105                 110
Pro Ile Phe Arg Gln Asn Trp Gly Asn Met Lys Ile His Lys Asn Phe
            115                 120                 125
Ser Ile Asp Leu Val Arg Asn Glu His Pro Thr Trp Asn Lys Lys Met
            130                 135                 140
Ile Glu Leu Glu Ala Ser Lys Arg Phe Glu Lys Tyr Ala Arg Phe Phe
145                 150                 155                 160
Met Glu Glu Thr Leu Lys Leu Ala Lys Lys Thr Arg Lys Gln Ala Asp
                165                 170                 175
Trp Gly Tyr Tyr Gly Tyr Pro Tyr Cys Phe Asn Met Ser Pro Asn Asn
            180                 185                 190
```

-continued

```
Leu Val Pro Glu Cys Asp Val Thr Ala Met His Glu Asn Asp Lys Met
        195                 200                 205

Ser Trp Leu Phe Asn Asn Gln Asn Val Leu Leu Pro Ser Val Tyr Val
    210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
        275                 280                 285

Gly Gly Asp Gly Ile Ile Ile Trp Gly Ser Ser Ser Asp Val Asn Ser
    290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330
```

CLONING AND RECOMBINANT PRODUCTION OF POLISTINAE VENOM ENZYMES, SUCH AS PHOSPHOLIPASE AND HYALURONIDASE, AND IMMUNOLOGICAL THERAPIES BASED THEREON

CROSS REFERENCE TO REALTED APPLICATIONS

The present application is a divisional of application Ser. No. 09/806,658, now U.S. Pat. No. 6,652,851 filed May 24, 2001, which is the U.S. national phase of international application No. PCT/US99/23211, filed Oct. 1, 1999, and which is a continuation-in-part of Ser. No. 09/166,205, filed Oct. 1, 1998, now U.S. Pat. No. 6,372,471.

FIELD OF THE INVENTION

The present invention is directed to nucleic acid molecules encoding Polistinae venom allergens, in particular enzymes such as phospholipase and hyaluronidase, or fragments thereof, recombinant vectors comprising such nucleic acid molecules, and host cells containing the recombinant vectors. The invention is further directed to expression of such nucleic acid molecules to produce a recombinant Polistinae venom enzyme, such as phospholipase or hyaluronidase, or recombinant fragments thereof. Such an allergen and fragments thereof are useful for diagnosis of allergy, for therapeutic treatment of allergy, for the treatment of immune system related diseases or disorders, or symptoms related thereto, and for the modulation of immune response towards an immunogen.

BACKGROUND OF THE INVENTION

Insect sting allergy to bees and vespids is of common occurrence. The vespids include hornets, yellow jackets and wasps (Golden, et al., 1989, Am. Med. Assoc. 262:240). Susceptible people can be sensitized on exposure to minute amounts of venom proteins; as little as 2–10 μg of protein is injected into the skin on a single sting by a vespid (Hoffman and Jacobson, 1984, Ann. Allergy. 52:276).

There are many species of hornets (genus *Dolichovespula*), yellow jackets (genus *Vespula*) and wasp (genus *Polistes*) in North America (Akre, et al., 1980, "Yellowjackets of America North of Mexico," Agriculture Handbook No. 552, US Department of Agriculture). The vespids have similar venom compositions (King, et al., 1978, Biochemistry 17:5165; King, et al., 1983, Mol. Immunol. 20:297; King, et al., 1984, Arch. Biochem. Biophys. 230:1; King, et al., 1985, J. Allergy and Clin. Immunol. 75:621; King, 1987, J. Allergy Clin. Immunol. 79:113; Hoffman, 1985, J. Allergy and Clin. Immunol. 75:611). Their venom each contains three major venom allergens, phospholipase (37 kD), hyaluronidase (43 kD) and antigen 5 (23 kD) of as yet unknown biologic function. U.S. Pat. No. 5,593,877 describes cloning and expression of the vespid venom allergens phospholipase and hyaluronidase. As described in this patent, the recombinant allergens permit expression of a protein or fragments thereof for use in immunotherapy, dignostics, and to investigate T and B cell allergens, it sets forth in greater detail the rationale for cloning vespid venom enzymes. However, unique vespid venom cDNAs were not described.

In addition to the insect venom allergens described above, the complete amino acid sequence of several major allergens from different grass (Perez, et al., 1990, J. Biol. Chem. 265:16210; Ansari, et al., 1989, Biochemistry 26:8665; Silvanovich, et al., 1991, J. Biol. Chem. 266:1204), tree pollen (Breiteneder, 1989, EMBO J. 8:1935; Valenta, et al., 1991, Science, 253:557), weed pollen (Rafnar, et al., 1991, J. Biol. Chem. 266:1229; Griffith, et al., 1991, Int. Arch. Allergy Appl. Immunol. 96:296), mites (Chua, et al., 1988, J. Exp. Med. 167:175), cat dander (Griffith, et al., 1992, Gene. 113:263), and mold (Aruda, et al., 1990, J. Exp. Med. 172:1529; Han, et al., 1991, J. Allergy Clin. Immunol. 87:327) have been reported in the past few years. These major allergens are proteins of 10–40 kD and they have widely different biological functions. Nearly all allergens of known sequences have a varying extent of sequence similarity with other proteins in our environment.

Although U.S. Pat. No. 5,593,877 provides for cloning and expression of vespid venom enzymes, particularly hyaluronidase and phospholipase, there remains a need to identify unusual and unexpected sequences for such enzymes, and to design effective expression systems for them. There is a particular need to delineate the B and helper T cell epitopes of the paper wasp (e.g., *Polistes annularis*). In particular, the major Polistinae venom allergens phospholipase and hyaluronidase are appropriate targets for determining the important B and T cell epitopes. In order to fully address the basis for allergic response to vespid allergens, and to develop allergen-based immunotherapies, the cDNA and protein sequences of several homologous allergens need to be investigated. Moreover, vectors suitable for high level expression in bacteria and eukaryotic cells of vespid allergens or their fragments should be developed. Recombinant vespid allergens and their fragments may then be used to map their B and T cell epitopes in the murine and, more importantly, human systems by antibody binding and T cell proliferation tests, respectively.

There is also a need in the art to use peptides having T or B cell epitopes of vespid venom allergens to study induction of tolerance in mice and induction of tolerance in humans.

There is a further need to test whether a modified peptide inhibits allergen T cell epitope binding to MHC class II molecule, or induces T cell anergy, or both.

Thus, there is a need in the art for unique sequence information about vespid venom allergens, and a plentiful source of such allergens for immunological investigations and for immunological therapy of the allergy.

Furthermore, due to the overuse of antibiotics throughout the world, and to the spread of numerous viruses, such as HIV, Ebolla, etc., efforts have been made to produce new "super" antibiotic medication, and compounds which have activity against viruses. For example, AZT has been developed, along with protease inhibitors to treat subjects suffering from HIV. However, the costs of developing new "super" antibiotics and anti-viral medications are enormous.

Hence, what is needed are agents and pharmaceutical compositions for treating immune system related diseases or disorders whose activity is not dependent necessarily on combating the particular virus or pathogen, but rather modulate or potentiate the immune system ability to combat the disease or disorder, thereby ameliorating the disease or disorder, or a symptom related thereto. Hymenoptera venoms, particularly vespid venoms, provide one possible source for such agents and pharmaceutical compositions, as described in U.S. Pat. Nos. 4,822,608 and 5,827,829.

The citation of references herein shall not be construed as an admission that such is prior art to the present invention.

SUMMARY OF THE INVENTION

The present invention provides a nucleic acid molecule encoding Polistinae venom enzymes, immunomodulatory fragments thereof, or derivatives or analogs thereof. In particular, the invention is directed to such nucleic acid molecules encoding a Polistinae venom phospholipase, and a Polistinae venom hyaluronidase. In specific embodiments, a nucleic acid molecule of the invention encodes an immunomodulatory portion of a T cell epitope of a Polistinae venom enzyme. In another embodiment, a nucleic acid molecule of the invention encodes an antigenic portion of a B cell epitope of a Polistinae venom enzyme.

The nucleic acids of the invention, which are not genomic, surprisingly are found, in one embodiment, to contain a non-coding, e.g., intronic sequences. In a specific embodiment, cDNA molecules for Polistinae venom enzyme contain what appears to be an intron. Thus, it has unexpectedly proved necessary to delete these "intronic" sequences in order to obtain a nucleic acid coding for a mature Polistinae venom enzyme, e.g., phosholipase or hyaluronidase.

Hence broadly, the present invention extends to an isolated nucleic acid molecule encoding a venom enzyme, conserved variant thereof, immunomodulatory fragment thereof, or derivative, or analog thereof. As noted above, the nucleic acid molecule contains internal non-coding sequences, i.e., in addition to 5⁻ and 3⁻ untranslated (UTR) sequences., but is not a genomic sequence. Examples of Polistinae venom enzymes which can be encoded by an isolated nucleic acid molecule of the invention include, but are not limited to phospholipase and hyaluronidase. Moreover, enzymes, conserved variants thereof, immunomodulatory fragments thereof, or analogs or derivatives thereof, from the venom of numerous Polistinae venoms can be encoded by an isolated nucleic acid molecule of the invention. A particular example comprises Polistinae of the genus *Polistes*, and particularly the species *annularis*.

In a particular embodiment, the present invention extends to an isolated nucleic acid molecule encoding a phospholipase $A_1$, conserved variants thereof, immunomodulatory fragments thereof, or analogs or derivatives thereof, from the genus *Polistes* and the species *annularis*, wherein the *P. annularis* has an amino acid sequence as depicted in SEQ ID NO:2, and more specifically, wherein the isolated nucleic acid molecule has a nucleotide sequence of SEQ ID NO:1, degenerate variants thereof, fragments thereof, or analogs or derivatives thereof.

In another particular embodiment, the present invention extends to an isolated nucleic acid molecule, that encodes hyaluronidase from *Polistes annularis* comprising an amino acid sequence of SEQ ID NO: 4, more particularly wherein the isolated nucleic acid has a nucleotide sequence of SEQ ID NO:3, degenerate variants thereof, fragments thereof, or analogs or derivatives thereof, conserved variants thereof, immunomodulatory fragments thereof, or analogs or derivatives thereof.

Moreover, the present invention extends to an isolated nucleic acid molecule hybridizable to an isolated nucleic acid molecule comprising a DNA sequence of SEQ ID NO:1 or 3, degenerate variants thereof, fragments thereof, or analogs or derivatives thereof.

Moreover, the present invention further extends to an isolated nucleic acid molecule encoding a Polistinae venom enzyme, or an immunomodulatory fragment, derivative or analog thereof, wherein the isolated nucleic acid molecule encodes an immunomodulatory portion of a T cell epitope or an antigenic portion of a B cell epitope of the Polistinae venom enzyme. Likewise, the present invention extends to an isolated polypeptide comprising an immunomodulatory portion of a T cell epitope of a Polistinae venom enzyme, wherein the polypeptide is encoded by an isolated nucleic acid molecule of the invention. Examples of waso venom enzymes for which isolated nucleic acid molecules of the present invention encode an immunomodulatory portion of a T cell epitope include, but certainly are not limited to, phospholipase and hyaluronidase. In a specific embodiment, the phospholipase $A_1$ and hyaluronidase originate from a genus *Polistes*, and particularly from the species *annularis*.

The invention further provides cloning vectors and expression vectors, which permit expression of the nucleic acids. Such vectors contain nucleic acids of the invention as set forth above. In the case of expression vectors, such nucleic acids are operatively associated with an expression control sequence.

The invention advantageously provides a method of producing a Polistinae venom phospholipase, conserved variant thereof, immunomodulatory fragment thereof, or analog or derivative thereof, which is encompassed by the present invention, comprises:

(a) culturing a host cell transformed with an expression vector comprising an isolated nucleic acid molecule hybridizable to an isolated nucleic acid molecule comprising a DNA sequence of SEQ ID NO:1, preferably having a sequence of SEQ ID NO:1, degenerate variants thereof, fragments thereof, or analogs or derivatives thereof, wherein the isolated nucleic acid molecule is operationally associated with a promoter, so that the Polistinae venom phospholipase, conserved variant thereof, immunomodulatory fragment thereof, or analog or derivative thereof, is produced by the host cell; and (b) recovering the Polistinae venom phospholipase, conserved variant thereof, immunomodulatory fragment thereof, or analog or derivative thereof so produced from the culture, the host cell, or both.

Another method is provided for producing a Polistinae venom hyaluronidase, conserved variants thereof, immunomodulatory fragments thereof, or analogs or derivatives thereof, comprises the steps of:

(a) culturing a host cell transformed with an expression vector comprising an isolated nucleic acid molecule hybridizable to an isolated nucleic acid molecule comprising a DNA sequence of SEQ ID NO:3, or preferably having a sequence of SEQ ID NO:3, degenerate variants thereof, fragments thereof, or analogs or derivatives thereof, wherein the isolated nucleic acid molecule is operationally associated with a promoter, so that the Polistinae venom hyaluronidase, conserved variant thereof, immunomodulatory fragment thereof, or analog or derivative thereof is produced by the host cell; and (b) recovering the Polistinae venom hyaluronidase, conserved variant thereof, immunomodulatory fragment thereof, or analog or derivative thereof so produced, from the culture, the host cell, or both.

In a particular example, the methods set forth above yield phospholipase $A_1$ or hyaluronidase of the genus *Polistes*, and particularly from the species *annularis*, wherein the phospholipase $A_1$ comprises an amino acid sequence of SEQ ID NO:2, conserved variants thereof, immunomodulatory fragments thereof, or analogs or derivatives thereof, and the hyaluronidase comprises an amino acid sequence of SEQ ID NO:4, conserved variants thereof, immunomodulatory fragments thereof, or analogs or derivatives thereof.

The present invention further extends to pharmaceutical compositions effective for the treatment of a venom allergen-specific allergic condition. In particular, the present invention extends to a pharmaceutical composition comprising a polypeptide encoded by an isolated nucleic acid molecule which encodes an immunomodulatory portion of a T cell or an antigenic portion of a B cell epitope of a Polistinae venom enzyme, e.g., phospholipase or hyaluronidase, and a pharmaceutically acceptable carrier thereof. Consequently, in a preferred embodiment, a pharmaceutical composition of the invention comprises an immunomodulatory T cell epitope of *Polistes annularis* venom phospholipase $A_1$, or hyaluronidase or an antigenic portion of a B cell epitope of *Polistes annularis* phospholipase $A_1$, or hyaluronidase.

Naturally, the present invention extends to a method for treating a vespid venom allergen-specific allergic condition comprising administering a therapeutically effective amount of a pharmaceutical composition of the invention, examples of which are set forth above. Administration of a pharmaceutical composition of the invention can occur parenterally, and particularly orally, pulmonarily, nasally, topically or systemically.

Furthermore, the present invention extends to use of a recombinant Polistinae venom enzyme of the invention in the manufacture of a medicament for, and an associated method for modulating an immune response towards an immunogen, e.g., treating a vespid allergic condition or treating an immune system related disease or disorder or a symptom of the immune system related disease or disorder. The polypeptide is encoded by an isolated nucleic acid molecule which encodes a Polistinae venom enzyme, wherein the polypeptide comprises an immunomodulatory fragment of a Polistinae venom enzyme. More particularly, an agent for treating an immune system related disease or disorder, or symptom related thereto, comprises a Polistinae venom enzyme or a vector that permits expression of the Polistinae venom or enzyme in vivo.

In a specific embodiment, the polypeptide is a phospholipase encoded by an isolated nucleic acid molecule hybridizable to, or preferably, comprising a DNA sequence of SEQ ID NO:1, degenerate variants thereof, fragments thereof, or analogs or derivatives thereof.

Hence, an agent for treating an immune system related disorder or disease, or a symptom thereof, comprises an isolated polypeptide encoded by an isolated nucleic acid molecule which encodes a Polistinae venom hyaluronidase, conserved variants thereof, immunomodulatory fragments thereof, or analogs or derivatives thereof.

In another embodiment, the polypeptide is a hyaluronidase encoded by an isolated nucleic acid molecule hybridizable to, and preferably comprising, a DNA sequence of SEQ ID NO:3, degenerate variants thereof, fragments thereof, or analogs or derivatives thereof.

Furthermore, the present invention extends to a pharmaceutical composition for modulating an immune response towards an immunogen, e.g., treating a vespid allergic condition or treating an immune system related disease or disorder or a symptom related thereto, wherein the pharmaceutical composition comprises a recombinant Polistinae venom enzyme and a pharmaceutically acceptable carrier thereof.

Administration of a pharmaceutical composition for treating an immune system related disease or disorder to a subject can be carried out parenterally, and particularly orally, pulmonarily, nasally, topically or systemically. Furthermore, numerous diseases or disorders related to the immune system can be treated with the present invention. Examples include, but are not limited to, a pathogenic disease or disorder such as a viral disease or disorder, e.g., HIV, Herpes Simplex virus, or papiloma virus; an autoimmune disease e.g. arthritis or Lupus; or a combination of such diseases or disorders.

It is a specific object of the invention to provide the surprising DNA sequence of isolated nucleic acid (cDNA) molecules that encode *Polistes annularis* hyaluronidase, conserved variants thereof, fragments thereof, or analogs or derivatives thereof.

It is still yet another object of the invention to provide amino acid sequences of *Polistes annularis* phospholipase $A_1$ and hyaluronidase, along with conserved variants thereof, fragments thereof, including immunomodulatory portions of T cell epitopes and antigenic portions of B cell epitopes of *Polistes annularis* phospholipase $A_1$ and hyaluronidase, either containing, or more preferably free, of "intronic" sequence. The deduced amino acid sequences of phospholipase $A_1$ and hyaluronidase from Pol a allow comparison of their homology to analogous enzymes from other vespids. This information provides a basis for evaluating cross-reactivity of the allergens, which can be important for allergic reactions and for therapeutic treatments. Hence, in a specific embodiment, the present invention enables one of ordinary skill in the art to determine and evaluate the degree of similarity of phospholipase $A_1$ and hyaluronidase of Pol a to environmental proteins and/or autologous proteins. It is believed that similarity of the vespid venom enzymes to such environmental proteins, and particularly to autologous proteins, has important implications for the allergic response.

It is yet still another object of the invention to provide expression and cloning vectors comprising an isolated nucleic acid molecule encoding *Polistes annularis* phospholipase $A_1$ and hyaluronidase, including fragments comprising an immunomodulatory portion of a T cell epitope or an antigenic portion of a B cell epitope of these Polistinae venom enzymes so that the isolated nucleic acid molecules can be reproduced and expressed.

Yet another object of the invention comprises production of Polistinae venom enzymes such as phospholipase and hyaluronidase, along with conserved variants thereof, immunomodulatory fragments thereof, or analogs or derivatives thereof, using expression vectors of the invention, despite the presence of intronic sequences in cDNA clones Yet still another object of the invention is to provide agents and pharmaceutical compositions for treating an allergen-specific allergic condition in a subject, wherein the agents and pharmaceutical composition comprise an isolated polypeptide encoded by an isolated nucleic acid molecules which encodes a Polistinae venom enzyme, such as phospholipase or hyaluronidase, particularly from *Polistes annularis*, wherein the polypeptide comprises an antigen portion of a B cell epitope, or an immunomodulatory portion of a T cell epitope of, a Polistinae phospholipase $A_1$ or hyaluronidase.

Yet still another object of the invention is to provide a method for treating a vespid venom allergen-specific allergy in a subject, wherein a pharmaceutical composition for treating an allergen-specific allergic condition is administered to the subject.

Yet still another object of the invention is to provide agents and pharmaceutical compositions comprising such agents that treat an immune system related disease or disorder in mammal, such as a pathogenic disease or disorder, a viral disease or disorder, an autoimmune disease or disorder, or a combination of immune system related diseases or disorders.

Still yet another object of the invention is to provide agents and pharmaceutical composition for modulating immune response towards an immunogen in a mammal. As a result, administration of such a pharmaceutical composition modulates the immune system's ability to recognize and attack the immunogen. In a particular embodiment, the ability of the immune system of the mammal to recognize and attack the immunogen is increased upon administration of the pharmaceutical composition relative to the ability of the subject's immune system to recognize and attack the immunogen prior to administration of a pharmaceutical composition of the invention.

ABBREVIATIONS

| | |
|---|---|
| Dol m *Dolichovespula maculata* | white face hornet |
| Dol a *D. arenaria* | yellow hornet |
| Pol a *Polistes annularis* | wasp |
| Pol e *P. exclamans* | wasp |
| Ves m *Vespula maculifrons* | yellow jacket |
| Ves v *V. vulgaris* | yellow jacket |
| PCR | polymerase chain reaction |
| RACE | rapid amplification of cDNA ends |
| TCR | T cell receptor for antigen |

BRIEF DESCRIPTION OF THE DRAWINGS

FIGS. 1A–B. The cDNA nucleotide sequence encoding Pol a venom phospholipase $A_1$ (SEQ ID NO:1) and the amino acid sequence of Pol a venom phospholipase $A_1$ (SEQ ID NO:2). Note that the first 18 amino acid residues of SEQ ID NO:2 represent a portion of a signal sequence. Hence, amino acid residue 19 of SEQ ID NO:2 (glycine) is the N-terminus amino acid residue in mature Pol a phospholipase $A_1$.

FIGS. 2A and 2B. Pol a phospholipase cDNA contains two introns. (A) The nucleotide sequence of papla intron 1 (SEQ ID NO:5), an intron in Pol a venom phospholipase $A_1$ cDNA located between nucleotides 111 and 112 of SEQ ID NO:1. (B) The nucleotide sequences of papla intron 2 (SEQ ID NO:6), an intron in Pol a venom phospholipase $A_1$ cDNA located between nucleotides 720 and 721 of SEQ ID NO:1.

FIGS. 3A–B. Amino acid residue sequence similarity among hornet venom phospholipase (SEQ ID NO:7), yellowjacket phospholipase (SEQ ID NO:8) and paper wasp phospholipase $A_1$ (SEQ ID NO:2).

FIGS. 4A–C. The cDNA nucleotide sequence encoding Pol a venom hyaluronidase (SEQ ID NO:3) and the amino acid sequence of Pol a hyaluronidase (SEQ ID NO:4). Note that the first 23 amino acid residues of SEQ ID NO:4 represent a portion of a signal sequence. Hence, amino acid residue 30 of SEQ ID NO:4 (serine) is the N-terminus amino acid residue of mature Pol a hyaluronidase.

FIG. 5. The nucleotide sequence of Pahya (SEQ ID NO:9), an intron in Pol a hyaluronidase cDNA, located between nucleotides 733 and 734 of SEQ ID NO:3.

FIGS. 6A–B. Amino acid residue sequence similarity among bee venom (bv) hyaluronidase (SEQ ID NO:10), Dol m (wfh) hyaluronidase (SEQ ID NO:11), Ves v (vv) hyaluronidase (SEQ ID NO:12), and Pol a (pa) hyaluronidase (SEQ ID NO:4).

DETAILED DESCRIPTION OF THE INVENTION

The present invention is directed to recombinant nucleic acid molecules encoding Polistinae venom enzymes, such as phospholipase and hyaluronidase, and immunomodulatory fragments, derivatives or analogs thereof, and polypeptides encoded by such nucleic acid molecules useful in the diagnosis and therapy of vespid venom-specific allergy. In specific embodiments, the present invention is directed to a recombinant nucleic acid molecule encoding an immunomodulatory fragment of a Polistinae phospholipase, in particular Pol a phospholipase $A_1$, immunomodulatory fragments thereof, analogs or derivatives thereof, and Pol a hyaluronidase, conserved variants thereof, immunomodulatory fragments thereof, and analogs or derivatives thereof.

The present invention is based, in part, on the surprising and wholly unexpected discovery of internal non-coding segments of cDNAs encoding both Pol a phospholipase and Pol a hyaluronidase. Prior to this discovery, cDNAs for vespid venom enzymes did not contain such apparent "intronic" sequences.

This discovery has two significant implications. The first is that Polistinae, and more particularly, *Polistes*, and more particularly still, Pol a, cDNAs appear to contain "introns". Thus, Polistinaes of this subfamily express unique mRNAs, have unique mRNA processing capabilities, and potentially represent interesting splice variants.

The term "introns" is used to refer to nucleic acid sequences that are not expected to be present in a cDNA coding for phospholipase or hyaluronidase, and that are not 5' or 3' UTR sequences. The sequences may represent unexpected splice variants of the proteins, incomplete processing of mRNAs, or some regulatory feature found in this subfamily, genus, and species of vespid.

The presence of these "intron" sequences significantly impacts preparation of expression vectors. While it is possible to express the unique polypeptides encoded by these cDNAs, in another embodiment an unpredictable modification of the cDNA is required to eliminate these "introns" in order to express mature forms of the Polistinae venom enzymes, e.g., for use in immunotherapy. Thus, it has unexpectedly proven necessary to further engineer coding sequences for Polistinae phospholipase and hyaluronidase. Once these "intron" sequences are deleted, phospholipase or hyaluronidase proteins comprising the natural amino acid sequence can be obtained.

The invention is further directed to expression vectors comprising such nucleic acid molecules, and to methods for producing Polistinae venom enzyme polypeptides of the invention by expressing such expression vectors and recovering the produced Polistinae venom enzyme polypeptides.

The invention also provides pharmaceutical compositions effective for the treatment of a vespid venom, and likely even a hymenoptera venom, allergen-specific allergic condition comprising a polypeptide of the invention, and methods for treating such allergic conditions comprising administering a therapeutically effective amount of the pharmaceutical compositions of the invention.

The polypeptides of the invention can also be useful for diagnosis of vespid, particularly Polistinae, venom-specific allergic conditions.

In addition, it has been discovered that, unexpectedly, administration of a pharmaceutical compositions comprising Polistinae venom phospholipase or hyaluronidase be used to treat an immune system related disease or disorder, such as a pathogenic disease or disorder, a viral disease or disorder, an autoimmune disease or disorder, or a combination of such diseases or disorders.

Accordingly, as used herein, the term "Polistinae venom allergen" refers to a protein found in the venom of a Polistinae, such as the paper wasp (*Polistes annularis*), to which susceptible people are sensitized on exposure to the sting of the insect. While most antigens are characterized by being reactive with specific IgG class antibodies, an allergen is characterized by also being reactive with IgE type antibodies. The IgE type antibodies are responsible for mediating the symptoms of an allergic condition, i.e., immediate-type hypersensitivity.

As used herein, the term "vespid" is used according to the practice of those in the field of allergy, and refers to insects belonging to the worldwide family of Vespidae, i.e., social wasps including hornets, yellowjackets, and paper wasps. In particular, vespids of the subfamily Vespinae include the subfamilies Vespinae and Polistinae. More particularly, the vespids of the subfamily include the genera *Vespa* Linnaeus, *Vespula* Thomson, *Dolichovespula* Rohwer, and *Polistes* Latreille. *Vespula* and *Dolichovespula* can be considered subgenera of the genus *Vespula* Species in the genus *Vespa* include but are not limited to *V. crabro* (L.) and *V. orientalis* (Linnaeus). Species in the genus *Vespula* include but are not limited to *V. germanica* (Fab.), *V. squamosa* (Drury), *V. maculifrons* (Buysson), *V. flavopilosa* (Jacobson), *V. vulgaris* (L.), and *V. pensylvanica* (Saussure). Species in the genus *Dolichovespula* include but are not limited to *P. dominulus*, *D. maculata* (L.) and *D. arenaria* (Fab.).

The subfamily Polistinae includes the genus *Polistes*. Species in the genus *Polistes* include but are not limited to *P. dominulus*, Pol a (Linnaeus), *P. exclamans* (Viereck), *P. metricus* (Say), *P. fuscatus* (Fabricius), *P. gallicus*, *pacificus*, *P. canadensis*, *P. kaibabensis*, *P. comanchus*, *P. commanchus*, *P. annularis*, *P. exclamans*, *P. instabilis*, *P. carnifex*, *P. major*, *P. metricus*, *P. perplexus*, *P. carolinus*, *P. flavus*, *P. fuscatus*, *P. aurifer*, *P. dorsalis*, *P. bellicosus*, *P. apachus*, *P. sulcifer*, *P. semenowi*, *P. atrimandibularis*, *P. biglumis*, *P. bischoffi*, *P. dominulus*, *P. nimpha*, *P. Pgallicus*, *P. associus*, *P. gigas*, *P. stigma*, *P. adustus*, *P. snelleni*, *P. mandarinus*, *P. chinensis*, *P. sulcatus*, *P. formosanus*, *P. japonicus*, *P. watttii*, *P. macaensis*, *P. jadwigae*, *P. olivaceus*, *P. rothneyi*, *P. jokohamae*, *P. poeyi*, *P. paraguayensis*, *P. rossi*, *P. cinctus*, *P. cavapyta*, *P. buysonni*, *P. brevifissus*, *P. ferreri*, *P. infuscatus*, *P. satan*, *P. melanotus*, *P. erythrocephalus*, *P. lanio*, *P. penai*, *P. aterrimus*, *P. huacapistana*, *P. versicolor*, *P. ninabamba*, *P. simillimus*, *P. adelphus*, *P. biguttatus*, *P. binotatus*, *P. consobrinus*, *P. peruvianus*, *P. weyrauchorum*, *P. xanthogaster*, *P. maranonensis*, *P. myersi*, *P. veracrucis*, *P. eburneus*, *P. stabilinus*, *P. pseudoculatus*, *P. apicalis*, *P. oculatus*, *P. crinitus*, *P. cubensis*, *P. minor*, *P. incertus*, *P. franciscanus*, *P. goeldii*, *P. olivaceus*, *P. bicolor*, *P. thoracicus*, *P. rufiventrus*, *P. moraballi*, *P. angulinus*, *P. subsericeus*, *P. testaceicolor*, *P. claripennis*, *P. billardieri*, *P. davillae*, *P. occipitalis*, *P. atrox*, *P. deceptor*, *P. niger*, *P. candidoi*, *P. geminatus*, *P. melanosoma*, *P. actaeon*, *P. obscurus*, *P. bequaertianus*, *P. cinerascens*, and *P. apachus* (Saussure).

As used herein, the term "phospholipase" refers to the class of enzymes that act on phospholipid substrates, e.g., to hydrolyze fatty acids. In a specific embodiment a phospholipase catalyzes rapid hydrolysis of the acyl group at position 1 of synthetic phosphatidylcholines, and a slow hydrolysis of the acyl group at position 2. Thus, the vespid phospholipases of the invention can have both $A_1$ and B types of phospholipase activities. The phospholipases of the invention can have low level lipase activity as well.

As used herein, the term "hyaluronidase" refers to the class of enzymes that act on the disaccharide unit of D-glucuronic acid and N-acetyl-D-glucosamine. Such enzymes mediate the hydrolysis of polymers of repeating disaccharides comprising D-glucuronic acid and N-acetyl-D-glucosamine. One example of such polymer is hyaluronic acid. Hyaluronidase catalyzes the release of reducing groups of N-acetylglucosamine from hyaluronic acid.

A "genomic" sequence contains all introns 5' and 3' untranslated sequences, and 5' and 3' untranscribed, (and often regulatory) sequences of a gene. Thus, a coding sequence is not genomic when it lacks one or more introns and 5' and 3' untranscribed sequences, particularly regulatory sequences.

As used herein, the term "immunomodulatory" refers to an ability to increase or decrease an antigen-specific immune response, either at the B cell or T cell level. Immunomodulatory activity can be detected e.g., in T cell proliferation assays, by measurement of antibody production, lymphokine production or T cell responsiveness. In particular, in addition to affects on T cell responses, the immunomodulatory polypeptides of the invention may bind to immunoglobulin (i.e., antibody) molecules on the surface of B cells, and affect B cell responses as well.

As used herein, the term "derivative" refers to a modified nucleic acid encoding a Polistinae, particularly a *Polistes*, phospholipase or hyaluronidase venom enzyme that contains a substitution, deletion, or insertion, and the protein encoded thereby. The term "derivative" specifically refers to a low IgE binding derivative (or analog) that contains amino acid substitutions at key amino acid residues, resulting in reduced IgE binding without disrupting the overall conformation or secondary and tertiary structure of the protein. Low IgE binding derivatives are described in PCT/DK99/00136.

As used herein, the phrase "immune system related disease or disorder" refers to a disease or disorder which evokes an immune response in a subject, or effects the ability of the immune system to respond to an immunogen. Hence, examples of immune system related diseases or disorders comprise a pathogenic disease or disorder; a viral disease or disorder, e.g. HIV, Herpes Simplex virus, or papiloma virus; an autoimmune disease, e.g. arthritis or Lupus.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acid molecules, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$ (about 60°), e.g., 40% formamide, with 5× or 6×SSC. High stringency hybridization conditions correspond to the highest $T_m$ (greater than or equal to about 65°), e.g., 50% formamide, 5× or 6×SSC. Hybridization requires that the two nucleic acid molecules contain complementary sequences, although depending on the stringency of the hybridization, mismatches between bases are possible. The appropriate stringency for hybridizing nucleic acid molecules depends on the length of the nucleic acid molecules and the degree of complementation, variables well known in the art. The greater the degree of similarity or homology between two nucleotide sequences, the greater the value of $T_m$ for hybrids of nucleic acid molecules having those sequences. The relative stability (corresponding to higher $T_m$) of nucleic acid hybridizations decreases in the following order: RNA: RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acid molecules, i.e., oligonucleotides, the position of mismatches becomes more important, and the length of the oligonucleotide determines its specificity (see Sambrook et al., supra, 11.7–11.8). Preferably a minimum length for a hybridizable nucleic acid molecule is at least about 10 nucleotides; preferably at least about 10 nucleotides; and more preferably the length is at least about 20 nucleotides; even more preferably 30 nucleotides; and most preferably 40 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that directs the host cell to transport the polypeptide to the cell surface or secrete the polypeptide into the media, and this signal peptide is usually selectively degraded by the cell upon exportation. Signal sequences can be found associated with a variety of proteins native to prokaryotes and eukaryotes.

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: a Laboratory Manual," Second Edition (1989) Cold Spring Harbor Laboratory Press, Cold Spring Harbor, N.Y. (herein "Sambrook et al., 1989"); "DNA Cloning: a Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "a Practical Guide To Molecular Cloning" (1984).

The present invention is based, in part, on the cloning and sequence determination of a Polistinae venom phospholipase and hyaluronidase. The cloning and sequence determination of this Polistinae venom enzymes is highly significant, since the cDNA clones unexpectedly contain extra nucleotide sequences that do not appear to encode polypeptide. Vespid venom allergic conditions are common, and in some sensitive individuals an allergic reaction can proceed to anaphylaxas, which is potentially fatal. As with vespids in general, Polistinae venom components are likely to play an important role in production of allergin. It is therefore of great importance that the nucleotide and amino acid sequence information for the Polistinae venom allergens is known so that accurate diagnostic information about the nature of the allergic condition, especially specific allergen sensitivities, can be determined and effective therapeutic treatments of the underlying allergic condition can be effected. It has unexpectedly been the casxe here, since Polistinae cDNAs were surprisingly found with non-transcribed sequences.

Isolation of a Nucleic Acid Molecule Encoding a Wasp Venom Enzyme

Isolation of nucleic acid molecules encoding vespid venom enzymes was fully described in U.S. Pat. No. 5,593,877. The present invention concerns the unexpected and surprising discoveries that Polistinae cDNAs contain "introns". Typically, introns are spliced out of mRNA and are, therefore, not usually found in cDNAs. The sequences may represent splice variants.

Derivatives of a Polistinae venom enzyme, fragments, and fusion proteins (see infra), are additionally provided, as well as nucleic acid molecules encoding the same.

In a preferred aspect, the present invention provides the complete nucleic acid sequence of a Polistinae venom enzyme. In particular, the present invention provides the nucleic acid sequence of a Polistinae phospholipase, in particular Pol a (paper wasp) phospholipase $A_1$, and hyaluronidase, in particular Pol a hyaluronidase.

In a specific embodiment, to obtain a nucleic acid molecule encoding a Polistinae venom enzyme, polymerase chain reaction (PCR) is combined with the rapid amplification of cDNA ends (RACE) technique described by Frohman et al. (Proc. Nat. Acad. Sci. USA, 1998, 85:8998–9002; see also Frohman, 1990, Amplifications: A Forum for PCR Users 5:11) to amplify a fragment encoding a sequence comprising the Polistinae venom enzyme prior to selection. Oligonucleotide primers representing a Polistinae venom enzyme of the invention can be used as primers in PCR. Generally, such primers are prepared synthetically. Sequences for such oligonucleotide primers can be deduced from amino acid sequence information. Such oligonucleotide sequences may be non-degenerate, but more frequently the sequences are degenerate. More preferably, the primers are based on the nucleic acid sequences for the Polistinae venom enzymes disclosed herein. The oligonucleotides may be utilized as primers to amplify by PCR sequences from a source (RNA or DNA), preferably a cDNA library, of potential interest. For example, PCR can be used to amplify a Polistinae venom enzyme coding sequence from a Polistinae acid gland cDNA library. PCR can be carried out, e.g., by use of a Perkin-Elmer Cetus thermal cycler and Taq polymerase (Gene Amp™).

The present invention further provides for isolating a homolog of a Polistinae venom enzyme from any species of Polistinae. One can choose to synthesize several different degenerate primers for use, e.g., in PCR reactions. It is also possible to vary the stringency of hybridization conditions used in priming PCR reactions, to allow for greater or lesser degrees of nucleotide sequence similarity between a homolog of a Polistinae venom enzyme and a specific Polistinae venom enzyme disclosed herein. After successful amplification of a segment of a homolog of a Polistinae venom enzyme, that segment may be cloned and sequenced, and utilized as a probe to isolate a complete cDNA or genomic clone. This, in turn, will permit the determination of the complete nucleotide sequence, the analysis of its expression, and the production of its protein product for functional analysis, as described infra. In this fashion, additional genes encoding Polistinae venom enzymes, in particular, phospholipases and hyaluronidases, may be identified and expressed.

In another embodiment, genes encoding a Polistinae venom enzyme can be isolated from a suitable library by screening with a probe. Useful probes for isolating a Polistinae venom enzyme gene can be generated from the sequence information provided herein.

An expression library can be constructed by methods known in the art. Preferably, a cDNA library is prepared from cells or tissues that express a Polistinae venom enzyme, i.e., cells from the poison gland located near the venom sac. Sometimes the poison gland is referred to as the acid gland. For example, mRNA or total RNA can be isolated, cDNA is made and ligated into an expression vector (e.g., a plasmid or bacteriophage derivative) such that it is capable of being expressed by the host cell into which it is then introduced. Various screening assays can then be used to select for the positive clones. For example, PCR with appropriate primers, which can be synthesized based on the sequences provided herein, can be used. PCR is preferred as the amplified production can be directly detected, e.g., by ethydium bromide staining. Alternatively, labeled probes derived from the nucleic acid sequences of the instant application can be used to screen the colonies. Although the poison (acid) gland can be difficult to isolate, and the quantity of mRNA problematic, specific PCR based on primers of the present invention can overocme these problems by permitting specific amplification of trace amounts of mRNA or cDNA or even genomic DNA.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for a Polistinae venom enzyme.

Some recombinant proteins expressed by bacteria, e.g., Polistinae venom hyaluronidases, may react with antibodies specific for the native proteins. Other bacterially expressed recombinant proteins, such as venom phospholipases, may not react with antibodies specific for the native protein. Thus, in cases where the recombinant proteins are immunoreactive, it is possible to select for positive clones by immunoblot.

In another embodiment, the specific catalytic activity of the enzyme, such as lipase activity of an expressed Polistinae venom phospholipase, can be used for selection. However, bacterially expressed eukaryotic proteins may not fold in an active conformation.

Generally, according to the present invention, any method of screening for positive clones can be used.

Alternatives to isolating the Polistinae venom enzyme genomic DNA or cDNA include, but are not limited to, chemically synthesizing the gene sequence itself from the sequence provided herein.

The above methods are not meant to limit the methods by which clones of a Polistinae venom enzyme may be obtained.

A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as various pBR322 derivatives, for example, pUC, CR, pGEX vectors, pmal-c, pFLAG, etc. The insertion into a cloning vector can, for example, be accomplished by ligating the DNA fragment into a cloning vector which has complementary cohesive termini. In a preferred aspect of the invention, the PCR amplified nucleic acid molecules of the invention contain 3'-overhanging A-nucleotides, and can be used directly for cloning into a pCR vector with compatible T-nucleotide overhangs (Invitrogen Corp., San Diego, Calif.). However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and a Polistinae venom enzyme gene may be modified by homopolymeric tailing. Recombinant molecules can be introduced into host cells via transformation, transfection, infection, electroporation, etc., so that many copies of the gene sequence are generated.

In specific embodiments, transformation of host cells with recombinant DNA molecules that incorporate the isolated Polistinae venom enzyme gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

Expression of a Polistinae Venom Allergen Polypeptide or Fragment

As pointed out above, the isolated nucleic acids encoding Polistinae venom enzymes, particularly *Polistes* venom proteins, contain unexpected sequences that should be absent for the cDNA to encode a protein similar to other Polistinae venom enzymes, e.g., as described in U.S. Pat. No. 5,593,877. In one embodiment, the "intron"-containing nucleic acids are expressed without further modification. In another embodiment, the nucleic acids are modified using the techniques described herein and exemplified infra, or as described in the references cited above, such as Sambrook et. al., to produce a protein having an amino acid sequence of a native Polistinae venom enzyme (though, as discussed below, such a protein may have a different secondary or tertiary structure, or include other polypeptide sequences fused to it).

The nucleotide sequence coding for a Polistinae venom enzyme, or an immunomodulatory fragment, derivative or analog thereof, can be inserted into an appropriate expression vector, i.e., a vector which contains the necessary elements for the transcription and translation of the inserted protein-coding sequence. Such elements are termed herein a "promoter." Thus, the nucleic acid molecule encoding the Polistinae venom enzyme is operationally associated with the promoter. An expression vector also preferably includes a replication origin. The necessary transcriptional and translational signals can also be supplied by the native gene encoding a Polistinae venom enzyme and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In an alternative embodiment, a recombinant Polistinae venom enzyme of the invention, or an immunomodulatory fragment, derivative or analog thereof, is expressed chromosomally, after integration of the Polistinae venom enzyme coding sequence by recombination. In this regard, any of a number of amplification systems may be used to achieve high levels of stable gene expression (See, Sambrook et al., 1989, supra, at Section 16.28).

The cell into which the recombinant vector comprising the nucleic acid molecule encoding the Polistinae venom enzyme is cultured in an appropriate cell culture medium under conditions that provide for expression of the Polistinae venom enzyme by the cell. The expressed Polistinae venom enzyme can then be recovered from the culture according to methods well known in the art. Such methods are described in detail, infra.

In a another embodiment, a Polistinae venom enzyme-fusion protein can be expressed. A Polistinae venom enzyme-fusion protein comprises at least a functionally active portion of a non-Polistinae venom enzyme protein joined via a peptide bond to at least an immunomodulatory portion of a Polistinae venom enzyme. The non-Polistinae venom enzyme sequences can be amino- or carboxyl-terminal to the Polistinae venom enzyme sequences. A recombinant DNA molecule encoding such a fusion protein comprises a sequence encoding at least a functionally active portion of a non-Polistinae venom enzyme joined in-frame to the coding sequence for a Polistinae venom enzyme. It may encode a cleavage site for a specific protease, e.g., Factor Xa, preferably at the juncture of the two proteins.

In another specific embodiment, a fragment of the Polistinae venom enzyme is expressed as a free (non-fusion) protein.

In a specific embodiment, the Polistinae venom phospholipase, and immunomodulatory fragments thereof, are expressed with an additional sequence comprising about six histidine residues, e.g., using the pQE12 vector (QIAGEN, Chatsworth, Calif.). The presence of the histidine makes possible the selective isolation of recombinant proteins on a Ni-chelation column.

In another embodiment, a periplasmic form of the fusion protein (containing a signal sequence) can be produced for export of the protein to the *Escherichia coli* periplasm. Export to the periplasm can promote proper folding of the expressed protein.

Any of the methods previously described in U.S. Pat. No. 5,593,877 for the insertion of DNA fragments into a vector may be used to construct expression vectors containing a gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Polistinae venom enzyme, or an immunomodulatory fragment thereof, may be regulated by a second nucleic acid sequence so that the Polistinae venom enzyme protein or peptide is expressed in a host transformed with the recombinant DNA molecule. For example, expression of a Polistinae venom enzyme protein may be controlled by any promoter/enhancer element known in the art, but these regulatory elements must be functional in the host selected for expression. Promoters which may be used to control Polistinae venom enzyme gene expression include, but are not limited to, the CMV immediate early promoter, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the enzyme protein expressed in bacteria may not be properly folded. Expression in yeast can produce a glycosylated product. Expression in insect cells can be used to increase the likelihood of "native" glycosylation and folding of a heterologous Polistinae venom enzyme. Furthermore, different vector/host expression systems may affect processing reactions, such as proteolytic cleavages, to a different extent. It is interesting to note that it has been observed that glycosylation and proper refolding are not essential for immunomodulatory activity of a Polistinae venom allergen since bacterial-produced allergen is active in a T cell proliferation assay.

Vectors are introduced into the desired host cells by methods known in the art, e.g., transfection, electroporation, electrotransfer, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263: 14621–14624; Hartmut et al., Canadian Patent Application No. 2,012,311, filed Mar. 15, 1990).

Preferred vectors, particularly for protein production in vivo, are viral vectors, such as lentiviruses, retroviruses, herpes viruses, adenoviruses, adeno-associated viruses, vaccinia viruses, baculoviruses, and other recombinant viruses with desirable cellular tropism. Thus, a vector encoding a Polistinae venom enzyme can be introduced in vivo or ex vivo using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and expression procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Examples of particular vectors include, but are not limited to, a defective herpes virus 1 (HSV1) vector (Kaplitt, et al., Molec. Cell. Neurosci. 2:320–330, 1991; International Patent Publication No. WO 94/21807, published Sep. 29, 1994; International Patent Publication No. WO 92/05263, published Apr. 2, 1994); an attenuated adenovirus vector, such as the vector described by Stratford-Perricaudet, et al. (J. Clin. Invest. 90:626–630, 1992; see also La Salle, et al., Science 259:988–990, 1993); and a defective adeno-associated virus vector (Samulski, et al., J. Virol. 61:3096–3101, 1987; Samulski, et al., J. Virol. 63:3822–3828, 1989; Lebkowski, et al., Mol. Cell. Biol. 8:3988–3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer, et al., Science 259:1745–1748, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Alternatively, non-viral DNA vectors for gene therapy can be introduced into the desired host cells by methods known in the art, e.g., electroporation, microinjection, cell fusion, DEAE dextran, calcium phosphate precipitation, use of a gene gun (ballistic transfection; see, e.g., U.S. Pat. Nos. 5,204,253, 5,853,663, 5,885,795, and 5,702,384 and see Sanford, TIB-TECH, 6:299–302, 1988; Fynan et al., Proc. Natl. Acad. Sci. U.S.A., 90:11478–11482, 1993; and Yang et al., Proc. Natl. Acad. Sci. U.S.A., 87:1568–9572, 1990), or use of a DNA vector transporter (see, e.g., Wu, et al., J. Biol. Chem. 267:963–967, 1992; Wu and Wu, J. Biol. Chem. 263:14621–14624, 1988; Hartmut, et al., Canadian Patent Application No. 2,012,311, filed Mar. 15, 1990; Williams, et al., Proc. Natl. Acad. Sci. USA 88:2726–2730, 1991).

Receptor-mediated DNA delivery approaches can also be used (Curiel, et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir, et al., C.P. Acad. Sci., 321:893, 1998; WO 99/01157; WO 99/01158; WO 99/01175).

Both cDNA and genomic sequences can be cloned and expressed.

It is further contemplated that the Polistinae venom enzymes of the present invention, or fragments, derivatives or analogs thereof, can be prepared synthetically, e.g., by solid phase peptide synthesis.

Isolation and Purification

Once the recombinant Polistinae venom enzyme protein is identified, it may be isolated and purified by standard methods including chromatography (e.g., ion exchange, affinity, and sizing column chromatography), centrifugation, differential solubility, or by any other standard technique for the purification of proteins.

In a particular embodiment, a Polistinae venom enzyme and fragments thereof can be engineered to include about six histidyl residues, which makes possible the selective isolation of the recombinant protein on a Ni-chelation column. In a preferred aspect, the proteins are further purified by reverse phase chromatography.

In another embodiment, in which recombinant Polistinae venom enzyme is expressed as a fusion protein, the non-Polistinae venom enzyme portion of the fusion protein can be targeted for affinity purification. For example, antibody specific for the non-Polistinae venom enzyme portion of the fusion protein can be immobilized on a solid support, e.g., cyanogen bromide-activated Sepharose, and used to purify the fusion protein. In another embodiment, a binding partner of the non-Polistinae venom enzyme portion of the fusion protein, such as a receptor or ligand, can be immobilized and used to affinity purify the fusion protein.

In one embodiment, a Polistinae venom enzyme-fusion protein, preferably purified, is used without further modification, i.e., without cleaving or otherwise removing the non-Polistinae venom enzyme-portion of the fusion protein. In a preferred embodiment, the Polistinae venom enzyme-fusion protein can be used therapeutically, e.g., to modulate an immune response.

In a further embodiment, the purified fusion protein is treated to cleave the non-Polistinae venom enzyme protein or portion thereof from the Polistinae venom enzyme. For example, where the fusion protein has been prepared to include a protease sensitive cleavage site, the fusion protein can be treated with the protease to cleave the protease specific site and release Polistinae venom enzyme.

In a particular embodiment of the present invention, such recombinant Polistinae venom enzymes include but certainly are not limited to those containing, as a primary amino acid sequence, all or part of the amino acid sequence substantially as depicted in FIG. 1 (SEQ ID NO: 2) or 4 (SEQ ID NO:4), as well as fragments and other derivatives, and analogs thereof.

Derivatives and Analogs of Polistinae Venom Enzymes

The invention further relates to derivatives and analogs of Polistinae venom enzymes. The production and use of derivatives and analogs related to Polistinae venom enzymes are within the scope of the present invention. The derivative or analog is immunomodulatory, i.e., capable of modulating an antigen-specific immune response. Moreover, analogs or derivatives of Polistinae venom enzymes, particularly phospholipase and hyaluronidase from *Polistes annularis*, can also be used to treat immune system related diseases or disorders, or a symptom related thereto. In another embodiment, the derivative or analog can bind to a Polistinae venom enzyme-specific immunoglobulin, including IgG and IgE. Derivatives or analogs of Polistinae venom enzyme can be tested for the desired immunomodulatory activity by procedures known in the art, including but not limited to the assays described infra.

In particular, Polistinae venom enzyme derivatives can be made by altering the nucleic acid sequences of the invention by substitutions, additions or deletions. Due to the degeneracy of nucleotide coding sequences, other DNA sequences which encode substantially the same amino acid sequence as a nucleic acid encoding a Polistinae venom enzyme may be used in the practice of the present invention. These include but are not limited to nucleotide sequences comprising all or portions of a gene encoding the Polistinae venom enzyme that are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a Polistinae venom enzyme, including altered sequences in which functionally equivalent amino acid residues are substituted for residues within the sequence resulting in a conservative amino acid substitution. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of Polistinae venom enzyme include but are not limited to those which are substantially homologous to a Polistinae venom enzyme or fragments thereof, or whose encoding nucleic acid is capable of hybridizing to a nucleic acid molecule encoding a Polistinae venom enzyme. Hybridization can occur under moderately stringent to highly stringent conditions, depending on the degree of sequence similarity, as is well known in the art.

The derivatives and analogs of the invention can be produced by various methods known in the art. The manipulations which result in their production can occur at the gene or protein level. For example, the nucleic acid sequence of the cloned Polistinae venom enzyme can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a Polistinae venom enzyme, care should be taken to ensure that the modified gene remains within the same translational reading frame as Polistinae venom enzyme, uninterrupted by translational stop signals.

Additionally, the gene encoding a Polistinae venom enzyme can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Manipulations of the recombinant Polistinae venom enzyme may also be made at the protein level. Included within the scope of the invention are recombinant Polistinae venom enzyme fragments or other derivatives or analogs which are differentially modified during or after translation, e.g., by glycosylation, acetylation, phosphorylation, amidation, reduction and carboxymethylation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In a particular embodiment, the Polistinae venom enzyme or immunomodulatory fragment thereof is expressed in an insect cell expression system, e.g., using a baculovirus expression vector. As pointed out above, this should yield "native" glycosylation and structure, particularly secondary and tertiary structure, of the expressed polypeptide. Native glycosylation and structure of the expressed polypeptide may be very important for diagnostic uses, since the enzyme specific antibodies detected in diagnostic assays will be specific for the native enzyme, i.e., as introduced by a sting from a vespid.

Activity Assays With Peptides of the Invention

Numerous assays are known in immunology for evaluating the immunomodulatory activity of an antigen. For example, the Polistinae venom enzyme proteins produced by expression of the nucleic acid molecules of the invention can be used in diagnostic assays for allergic diseases, which are described in detail, infra. In general, such proteins can be tested for the ability to bind to antibodies specific for the enzyme. Preferably, such antibodies that are detected in the diagnostic assay are of the IgE class. However, it is important to note that natural allergen-specific antibodies have been found to bind weakly to denatured vespid venom allergens. Polistinae venom enzymes produced in eukaryotic expression systems, and particularly insect cell expression systems, may have the correct structure for antibody binding. Polistinae venom enzymes expressed in bacterial expression systems may not, and would thus require refolding prior to use in a diagnostic assay for antibody binding.

In another embodiment, the proteins of the invention can be tested in a proliferation assay for T cell responses. For such T cell response assays, the expression system used to produce the enzyme does not appear to affect the immunomodulatory activity of the protein. Generally, lymphocytes from a sensitized host are obtained. The host can be a mouse that has been immunized with a Polistinae venom enzyme, such as a Polistinae venom phospholipase or hyaluronidase that has been produced recombinantly according to the present invention.

In a preferred embodiment, peripheral blood leukocytes are obtained from a human who is sensitive to vespid venom. Using techniques that are well known in the art, T lymphocyte response to the protein can be measured in vitro. In a specific embodiment, infra, T cell responses are detected by measuring incorporation of $^3$H-thymidine, which increases with DNA synthesis associated with proliferation.

Cell proliferation can also be detected using an MTT assay (Mossman, 1983, J. Immunol. Methods 65:55–63; Niks and Otto, 1990, J. Immunol. Methods 130:140–151). Any method for detecting T cell proliferation known in the art can be used with the Polistinae enzyme produced according to the present invention.

Similarly, lymphokine production assays can be practiced according to the present invention. In one embodiment, lymphokine production can be assayed using immunological or co-stimulation assays (see, e.g., Fehlner et al., 1991, J. Immunol. 146:799) or using the ELISPOT technique (Czerkinsky, et al., 1988, J. Immunol. Methods 110:29). Alternatively, mRNA for lymphokines can be detected, e.g., by amplification (see Brenner, et al., 1989, Biotechniques 7:1096) or in situ hybridization (see, e.g., Kasaian and Biron, 1989, J. Immunol. 142:1287). Of particular interest are those individuals whose T cells produce lymphokines associated with IgE isotype switch events, e.g., IL-4 and IL-5 (Purkeson and Isakson, 1992, J. Exp. Med. 175:973–982). Also of interest are the polypeptide fragments of the Polistinae venom enzyme that contain epitopes recognized by T cells involved in IgE switch events.

Thus, in a preferred aspect, the proteins produced according to the present invention can be used in in vitro assays with peripheral blood lymphocytes or, more preferably, cell lines derived from peripheral blood lymphocytes, obtained from vespid venom enzyme sensitive individuals to detect secretion of lymphokines ordinarily associated with allergic responses, e.g., IL-4. Such assays may indicate which venom component or components are responsible for the allergic condition. More importantly, the fragments of the Polistinae venom enzyme can be tested. In this way, specific epitopes responsible for T cell responses associated with allergic response can be identified. The sequences of such epitopes can be compared to other vespid venom enzymes and to environmental or autologous proteins to determine if there are sequence similarities that suggest possible cross-reactivity. The peptides can be tested for the ability to induce T cell anergy, e.g., by mega-dose administration, modification to produce an epitope antagonist, administration in the absence of the appropriate costimulatory signals, and other methods thought to result in T cell anergy. Peptides containing such epitopes are ideal candidates for therapeutics.

In a further embodiment, the polypeptides of the invention can be used directly in assays to detect the extent of cross-reactivity with other environmental proteins and/or homologous proteins, with which they share sequence similarity. In particular, the fragments of the Polistinae venom enzymes that have sequence similarity with such environmental, and more particularly, homologous proteins can be evaluated for cross reactivity with antibodies or T cell specific for such proteins. In a specific embodiment, the cross reactivity of Polistinae venom phospholipases with human lipases can be evaluated. In another specific embodiment, the cross reactivity of Polistinae venom hyaluronidase with the sperm membrane protein PH-20 is evaluated.

Diagnostic and Therapeutic Uses of the Polistinae Venom Enzyme Polypeptides

The present invention provides a plentiful source of a pure Polistinae venom enzyme, or fragments, derivatives or analogs thereof, produced by recombinant techniques. Alternatively, given the sequence information provided by the present invention, polypeptide fragments, derivatives or analogs of the Polistinae venom enzymes can advantageously be produced by peptide synthesis.

The invention contemplates use of Polistinae venom enzymes, or immunomodulatory fragments, derivatives or analogs thereof for the preparation of diagnostic or therapeutic compositions, for the use in the diagnosis and therapy of vespid venom allergen-specific allergic conditions, treating vespid venom allergen-specific allergic conditions, treating immune system related conditions, and modulating immune response in a mammal against an immunogen. In particular, *Polistes* phospholipase, more particularly Pol a phospholipase $A_1$, or *Polistes* hyaluronidase, in particular Pol a hyaluronidase, or immunomodulatory fragments, derivatives or analogs of phospholipase or hyaluronidase, are contemplated for use in diagnosis, therapy, treatment, and modulation of immune response according to the present invention.

Diagnostic Methods

As use herein, the term diagnostic includes in vitro and in vivo diagnostic assays. Generally, such assays are designed to measure the activity of IgE antibodies specific for a given allergen. Such diagnostic assays depend heavily on the availability of pure allergen. This is especially true for determining sensitivity to a specific allergen component of a vespid venom. In vitro diagnostic assays for enzyme sensitivity include radioimmunoassay (RIA), immunoradiometric immunoassay (IRMA), radio-allergosorbent tests (RAST), enzyme-linked immunosorbent assay (ELISA), ELISPOT, magnetic allergosorbent assay, immunoblots, histamine release assays, and the like.

In a further embodiment, the present invention provides for determining the presence of epitopes that are predominantly reactive with IgE antibodies, or with other isotypes, e.g., IgG. Such epitopes may overlap or be distinct. In particular, fragments of the Polistinae venom enzymes of the invention can be used to identify such specific B cell epitopes. Identification of specific epitopes can provide a basis for developing therapies, as described infra.

The present invention contemplates in vitro diagnostic assays on peripheral blood lymphocytes, as described supra. Such diagnostic assays can give detailed information about the enzyme-specific T cell responses, the phenotype of the T cell response, and preferably the T cell epitope of the enzyme involved in T cell responses. The immunodominant epitope and the epitope involved in IgE isotype class switch events can be detected, if they are not the same. In particular, the T cell epitopes of Polistinae venom enzymes that stimulate proliferation and/or lymphokine secretion of T cells of a phenotype associated with IgE isotype class switching events can be identified for a specific individual, or for a class of individuals who share MHC haplotype or a predominant T cell receptor variable region expression, or both.

In vivo assays for allergenicity generally consist of skin prick sensitivity assays, in which serially diluted amounts of an allergen are administered either subcutaneously or intradermally into a patient's skin, and wheel and erythema reactions are detected. As with in vitro assays, the availability of pure venom enzyme greatly increases the value of the results of the in vivo diagnostic assays since cross-reactivity with impurities in extracts prepared from vespid venom sacs can be avoided.

Therapeutic Methods

Therapeutic compositions of the invention (see, infra) can be used in immunotherapy, also referred to as hyposensitization therapy. Immunotherapy has proven effective in allergic diseases, particular insect allergy. Allergens are administered parenterally over a long period of time in gradually increasing doses. Such therapy may be particularly effective when the allergen or allergens to which the patient is sensitive have been specifically identified and the therapy is targeted to those allergen(s). Thus, the availability of pure Polistinae venom enzyme in large quantities is important for immunotherapy of allergy.

In another embodiment, the present invention contemplates use of polypeptides comprising at least an immunomodulatory T cell epitope of a Polistinae venom enzyme to induce specific T cell allergy to a vespid venom enzyme. Identification of such peptides is described supra. More preferably, a peptide comprising such a T cell epitope and lacking a B cell epitope can be administered to a patient. The presence of B cell epitopes on an allergen can cause an undesirable systemic reaction when the allergen is used for immunotherapy. Thus, a particular advantage of the invention is the capability to provide allergen polypeptides that do not cause undesirable systemic effects.

In one embodiment, one or more polypeptide fragments can be injected subcutaneously to decrease the T cell response to the entire molecule, e.g., as described by Brine et al. (1993, Proc. Natl. Acad. Sci. U.S.A. 90:7608–12).

In another embodiment, one or more polypeptide fragments can be administered intranasally to suppress allergen-specific responses in naive and sensitized subjects (see e.g., Hoyne et al., 1993, J. Exp. Med. 178:1783–88).

Administration of a Polistinae venom enzyme peptide of the invention is expected to induce anergy, resulting in cessation of allergen-specific antibody production or allergen-specific T cell response, or both, and thus, have a therapeutic effect.

In a preferred aspect of the invention, peptide based therapy to induce T cell anergy is customized for each individual or a group of individuals. Using the diagnostic methods of the present invention, the specific T cell epitope or epitopes of a vespid venom enzyme involved in the allergic response can be identified. Peptides comprising these epitopes can then be used in an individualized immunotherapy regimen.

Treatment of Immune System Related Diseases or Disorders, or a Symptom Related Thereto As explained above, the present invention relates to polypeptides for treating immune system related diseases or disorders, or for modulating immune response in a mammal towards an immunogen, wherein the polypeptides are encoded by isolated nucleic acid molecules which encode Polistinae venom enzymes, such phospholipase $A_1$ and hyaluronidase from *Polistes annularis*, to name only a few. In particular, components of vespid venom, particularly phospholipase and hyaluronidase, have applications in modulating a subject's immune response to various immunogens, such as pathogens and viruses, to name only a few. In a particular embodiment, components of a Polistinae venom, and particularly phospholipase $A_1$ and hyaluronidase from *Polistes annularis* and conserved variants thereof, fragments thereof, or analogs or derivatives thereof modulate a subject's immune system to have increased ability to combat pathogens and viruses including, but not limited to, HIV, Herpes Simplex virus, or papilloma virus. In a specific embodiment, such a method comprises administering to a subject a therapeutically effective amount of a pharmaceutical composition comprising a polypeptide encoded by an isolated nucleic acid molecule comprising a DNA sequence of SEQ ID NOs: 1 or 3, degenerate variants thereof, fragments thereof, or analogs or derivatives thereof, or an isolated nucleic acid molecule hybridizable thereto, wherein the polypeptide comprises an antigenic portion of a B cell epitope or an immunomodulatory portion of a T cell epitope of *Polistes annularis* phospholipase $A_1$ or hyaluronidase.

Furthermore, it has been discovered that components of Polistinae venom, such as phospholipase $A_1$ and hyaluronidase of *Polistes annularis*, to name only a few, also have applications in treating an immune system related disease or disorder, or a symptom related thereto. As used herein, the phrase "immune system related disease or disorder" refers to a disease or disorder which evokes an immune response in a subject, or effects the ability of the immune system to respond to an immunogen. Examples of immune system related diseases or disorders which can be treated with agents and pharmaceutical compositions of the invention include, but are not limited to, a pathogenic disease or disorder; a viral disease or disorder, e.g. HIV, Herpes Simplex virus, or papilloma virus; or an autoimmune disease, e.g. arthritis or Lupus. Hence, the present invention encompasses agents for treating an immune system related disease or disorder, or a symptom related thereto, in a specific embodiment comprising an isolated polypeptide encoded by an isolated nucleic acid molecule comprising a DNA sequence of SEQ ID NOS:1 or 3, degenerate variants thereof, fragments thereof or analogs or derivatives thereof, wherein the isolated polypeptide comprises an immunomodulatory portion of a T cell epitope or an antigenic portion of a B cell epitope of *Polistes annularis* phospholipase $A_1$ or hyaluronidase.

Hence, naturally, the present invention extends to pharmaceutical compositions for treating an immune system related disease or disorder, comprising a Polistinae venom enzyme, degenerate variants thereof, fragments thereof., or analogs or derivatives thereof. Moreover, the present invention extends to a method for treating an immune system related disease or disorder, or a symptom related thereto, comprising administering a therapeutically effective amount of a pharmaceutical composition for treating an immune system related disease or disorder to a subject. The phrase "therapeutically effective amount" is used herein to mean an amount sufficient to treat, and preferably increase by at least about 30 percent, more preferably by at least 50 percent, most preferably by at least 90 percent, the ability of the immune system of a subject to combat effectively an immunogen. As further studies are conducted, information will emerge regarding appropriate dosage levels for modulation of immune system response towards an immunogen in various patients, and the ordinary skilled worker, considering the therapeutic context, age and general health of the recipient, will be able to ascertain proper dosing. Delivery can be of the protein or a gene therapy vector. Hence, for example, should the immune system related disease or disorder involve HIV, a clinically significant change would, for example, involve an increase in white blood cell count in a subject to whom a pharmaceutical composition of the invention is administered relative to white blood cell count prior to administration. Other such examples of monitoring a clinically significant change in a subject will be readily apparent to one of ordinary skill in the art. Furthermore, as further studies are conducted, information will emerge regarding appropriate dosage levels for treating an immune system related disease or disorder, or a symptom related thereto in various patients, and the ordinary skilled worker, considering the therapeutic context, age and general health of the recipient, will be able to ascertain proper dosing. Examples of pharmaceutically acceptable compositions are described infra.

Pharmaceutically Acceptable Compositions

The in vivo diagnostic or therapeutic compositions of the invention may also contain appropriate pharmaceutically acceptable carriers, excipients, diluents and adjuvants. As used herein, the phrase "pharmaceutically acceptable" preferably means approved by a regulatory agency of a government, in particular the Federal government or a state government, or listed in the U.S. Pharmacopeia or another generally recognized pharmacopeia for use in animals, and more particularly in humans. Suitable pharmaceutical carriers are described in "Remington's Pharmaceutical Sciences" by E. W. Martin.

Such pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Such compositions will contain an effective diagnostic or therapeutic amount of the active compound together with a suitable amount of carrier so as to provide the form for proper administration to the patient. While intravenous injection is a very effective form of administration, other modes can be employed, such as by injection, or by oral, nasal or parenteral administration.

The invention will be further clarified by the following examples, which are intended to be purely exemplary of the invention.

EXAMPLE 1

Paper Wasp Phospholipase

Based, in part, on the methods and disclosure of U.S. Pat. No. 5,593,877, nucleic acids encoding Pol a (paper wasp) phospholipase were obtained. However, these nucleic acids surprisingly include internal sequences that do not code for an amino acid sequence found as expected on the native protein. Although the nucleic acids described in this Example are cDNAs, and are not genomic, they appear to include "introns".

Materials and Methods

The methods used are the same as those described in U.S. Pat. No. 5,593,877 using RACE.

Results

When examining paper wasp phospholipase $A_1$ cDNA produced with RACE, it was observed that its length was longer than necessary to encode paper wasp phospholipase $A_1$ protein. It was discovered that, surprisingly, this augmented length was the result introns incorporated into the paper wasp phospholipase $A_1$ cDNA. Such a discovery was unexpected in light of studies conducted on the cDNAs of other vespid venoms, which invariably do not contain any introns. For example, the phospholipase cDNAs of yellow-jacket and hornet contain no such introns.

Because of this major unforeseen difference between paper wasp phospholipase $A_1$ cDNA and other vespid venom phospholipase cDNAs, special biotechniques and steps were required to isolate paper wasp phospholipase $A_1$ cDNA, which were not needed to obtain the venom phospholipase cDNA from other vespids, such as hornet and yellowjacket. In particular, in order to isolate the cDNA sequence encoding phospholipase $A_1$ for paper wasp, it was necessary to determine the size and location and number of introns.

Using the amino acid sequence derived from the cyanogen bromide degradation of paper wasp phospholipase $A_1$, the genetic code, and the nucleotide sequence of wasp phospholipase cDNA derived from the RACE protocol, two introns were discovered. The first intron, hereinafter referred to as "papla intron 1" comprises a nucleotide sequence as set forth in SEQ ID NO:5 (FIG. 2A). Papla intron 1 comprises 114 nucleotides, and is normally located between nucleotides 111 and 112 of the cDNA sequence encoding phospholipase $A_1$, set forth In SEQ ID NO:1.

A second intron, hereinafter referred to as "papla intron 2" was also discovered. This intron comprises a nucleotide sequence as set forth in SEQ ID NO:6 (FIG. 2B). Papla intron 2 contains 127 nucleotides, and is normally located between nucleotides 720 and 721 of SEQ ID NO:1.

In order to isolate the cDNA sequence encoding paper wasp phospholipase $A_1$ (SEQ ID NO:1), these introns had to be removed from the paper wasp phospholipase $A_1$ cDNA derived from RACE without disturbing the reading frame of the coding nucleotides. In essence, paper wasp phospholipase $A_1$ cDNA had to be re-designed so that only encoding nucleotides would be included. This re-design process was technically very difficult because, should one encoding nucleotide be accidentally removed along with an intron, or should one non-coding nucleotide not be removed, a reading frame shift would be produced which would result in mutations and could cause premature termination of the expression of the cDNA.

In this re-design process, specially designed oligonucleotides were chemically synthesized, each complementary to coding nucleotides located 5' and 3' of one of the introns. The amplified paper wasp phospholipase $A_1$ cDNA derived from RACE was then cloned into a self-replicating plasmid. This plasmid was denatured, and, under low stringency conditions, the oligonucleotides were permitted to anneal to the paper wasp phospholipase $A_1$ cDNA, leaving the introns single stranded. These oligonucleotides then served as primers for DNA synthesis, which generated a double stranded plasmid wherein the introns were deleted from one of the strands. A cell was then transfected with the plasmid using methods described above, and the cell was then cloned. Since one of the two DNA strands in the original plasmid had the introns deleted, half of the transfected cells contained a double stranded plasmid in which the introns had been removed. The cloned were then screened to isolate the cells having the plasmid comprising paper wasp cDNA comprising a DNA sequence of SEQ ID NO:9 (without introns). Copies of the particular plasmid were then isolated and sequenced to confirm the deletion of the introns. The re-designed paper wasp phospholipase $A_1$ cDNA was then removed from the particular plasmid, sequenced, amplified, and cloned into an expression vector, using the procedures described in Example 1 and in application Ser. No. 08/474, 853 and in U.S. Pat. No. 5,593,877, which are hereby incorporated by reference in their entireties.

A comparison of the deduced amino acid sequence of paper wasp phospholipase $A_1$ (SEQ ID NO:2) with other vespid venom phospholipases was performed. In particular, SEQ ID NO:2 was compared with phospholipase from white face hornet (*D. maculata*) (SEQ ID NO:7) and phospholipase from yellow jacket (*V. vulgaris*) (SEQ ID NO:8). The results of this sequence comparison are shown in FIG. 3.

EXAMPLE 2

Paper Wasp Hyaluronidase

Using the procedures described in U.S. Pat. No. 5,593, 877, the cDNA sequence encoding paper wasp (Pol a) hyaluronidase (SEQ ID NO:3) and its corresponding amino acid sequence (SEQ ID NO:4) were isolated and are set forth in FIG. 4. Nucleotides 449 through 536 of SEQ ID NO:3 encode a portion of a signal sequence. Hence, the amino acid residue at the N terminus of mature Pol a hyaluronidase is serine, which is encoded by nucleotides 536, 537, and 538.

Surprisingly, paper wasp hyaluronidase cDNA produced from the RACE protocol set forth above had greater length than necessary to encode Pol a hyaluronidase protein. Hence, it was concluded paper wasp hyaluronidase cDNA contained at least one intron. The presence of the at least one intron within the wasp hyaluronidase cDNA was unexpected in light of studies on hyaluronidase cDNA from other vespid venoms, such as yellowjacket and hornet, which do not contain introns. As a result, special biotechniques similar to those employed to isolate paper wasp phospholipase $A_1$ cDNA, and set forth in Example 3 supra, were required to isolate the cDNA encoding sequence of paper wasp hyaluronidase.

Initially, a determination was made as to the location and size of the introns within the paper wasp hyaluronidase cDNA. Once the introns were located, they had to be removed in such a manner as not to disturb any coding nucleotides. Hence, just as with paper wasp phospholipase $A_1$ cDNA, it was necessary to re-design paper wasp hyaluronidase cDNA so that only encoding nucleotides would be included. This re-design process was technically very difficult because, should one encoding nucleotide be accidentally removed along with an intron, or should one non-coding nucleotide not be removed, a missense frameshift mutation would be placed into the wasp hyaluronidase cDNA.

The cDNA encoding mature paper wasp hyaluronidase (SEQ ID NO:3) was prepared using procedure similar to that used to isolate the cDNA encoding paper wasp phospholipase $A_1$ supra, The cDNA without introns was then sequenced, amplified, and cloned into an expression vector, again using the procedures described above.

Paper wasp hyaluronidase cDNA was found to contain one intron. This intron, hereinafter referred to as "pahya", is 94 nucleotides long, and has a nucleotide sequence as set forth in SEQ ID NO:9 (FIG. 5). Normally, this intron is located between nucleotides 733 and 734 of SEQ ID NO:3.

A comparison of the amino acid sequence of paper wasp hyaluronidase (SEQ ID NO:4) with other vespid venom phospholipases was performed. In particular, SEQ ID NO:4 was compared with hyaluronidase from bee venom (SEQ ID NO:10), hyaluronidase from white face hornet (*D. maculata*) (SEQ ID NO:11) and hyaluronidase from yellowjacket (*V. vulgaris*) (SEQ ID NO:12). The results of this sequence comparison are shown in FIG. 15.

The present invention is not to be limited in scope by the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides and molecular weights for all biomolecules are approximate and are used for the purpose of description.

Various patents, references, procedures, and other documents are cited herein, the disclosures of which are incorporated by reference herein in their entirety.

What is claimed:

1. A recombinant Polistinae venom phospholipase comprising an amino acid sequence of SEQ ID NO.: 2.

2. The recombinant Polistinae venom phospholipase of claim 1 encoded by an isolated nucleic acid having a nucleotide sequence of SEQ ID NO.: 1.

3. The recombinant Polistinae venom phospholipase of claim 1, which is a fusion protein.

4. The recombinant Polistinae venom phospholipase fusion protein of claim 3 expressed by a bacterial or a yeast cell.

5. The recombinant Polistinae venom phospholipase fusion protein of claim 3 comprising a cleavage site for a specific protease.

6. The recombinant Polistinae venom phospholipase fusion protein of claim 3 comprising a polyhistidine sequence.

7. A pharmaceutical composition for modulating an immune response towards an immunogen in a mammal comprising the recombinant Polistinae venom phospholipase of claim 3 and a pharmaceutically acceptable carrier.

8. A method for modulating a vespid venom allergen-specific allergic condition in a mammal comprising admin istering to said mammal the recombinant Polistinae venom phospholipase of claim 3.

9. The method of claim 8, wherein the allergic condition is an allergy to vespid venom phopholipase.

10. The method of claim 8, wherein the allergic condition is an allergy to hymenoptera venom.

11. The method of claim 8, wherein the recombinant Polistinae venom phospholipase is administered orally, pulmonarilly, nasally or topically.

12. A method for modulating a vespid venom allergen-specific allergic condition in a mammal comprising administering to said mammal the recombinant Polistinae venom phospholipase of claim 1.

13. The method of claim 12, wherein the allergic condition is an allergy to vespid venom.

14. The method of claim 12, wherein the allergic condition is an allergy to hymenoptera venom.

15. The method of claim 12, wherein the recombinant Polistinae venom phospholipase is administered orally, pulmonarilly, nasally or topically.

* * * * *